United States Patent
Hadjiyski

(10) Patent No.: US 10,420,943 B2
(45) Date of Patent: Sep. 24, 2019

(54) SYSTEM AND METHOD FOR INTERLEAVED NEUROSTIMULATION

(71) Applicant: ADVANCED NEUROMODULATION SYSTEMS, INC., Plano, TX (US)

(72) Inventor: Banko I. Hadjiyski, Friendswood, TX (US)

(73) Assignee: Advanced Neuromodulation Systems, Inc., Plano, TX (US)

( * ) Notice: Subject to any disclaimer, the term of this patent is extended or adjusted under 35 U.S.C. 154(b) by 0 days.

(21) Appl. No.: 16/030,641

(22) Filed: Jul. 9, 2018

(65) Prior Publication Data

US 2018/0318587 A1 Nov. 8, 2018

Related U.S. Application Data

(63) Continuation of application No. 15/183,577, filed on Jun. 15, 2016, now abandoned.

(51) Int. Cl.
*A61N 1/36* (2006.01)
*A61N 1/05* (2006.01)

(52) U.S. Cl.
CPC ....... *A61N 1/36167* (2013.01); *A61N 1/0551* (2013.01); *A61N 1/0553* (2013.01); *A61N 1/36178* (2013.01); *A61N 1/36185* (2013.01)

(58) Field of Classification Search
CPC .......... A61N 1/36167–36178; A61N 1/36189; A61N 1/36196; A61N 1/3605
See application file for complete search history.

(56) References Cited

U.S. PATENT DOCUMENTS

| | | | | |
|---|---|---|---|---|
| 2006/0259099 | A1* | 11/2006 | Goetz | A61N 1/36071 607/66 |
| 2010/0191307 | A1* | 7/2010 | Fang | A61N 1/0551 607/46 |
| 2011/0054567 | A1* | 3/2011 | Lane | A61N 1/08 607/59 |
| 2014/0094871 | A1* | 4/2014 | Trier | A61N 1/36125 607/46 |

\* cited by examiner

*Primary Examiner* — George R Evanisko

(57) ABSTRACT

A system and method are provided to deliver interleaved stimulation to nerve tissue of interest. The system and method comprises an array of stimulation electrodes. The array is configured to be implanted proximate to nerve tissue of interest. An implantable medical device (IMD) is coupled to the array. The IMD includes memory storing a composite resultant pulse (CRP) sequence comprising first and second component sequences of first and second resultant pulse trains, respectively. One or more pulses from at least one of the first or second component sequences are temporally shifted relative to a corresponding target component sequence. The IMD further comprises a pulse generating circuit and switching circuit coupled to an output of the pulse generating circuit and the array. The switching circuit is configured to connect the pulse generating circuit to different combinations of the electrodes. The IMD further comprises a processor, configured to execute program instructions stored in the memory, directs the pulse generating circuit to generate the CRP sequence and manages the switching circuit to deliver the pulses of the first and second component sequences, in an interleaved manner, to first and second electrode combinations, respectively.

5 Claims, 15 Drawing Sheets

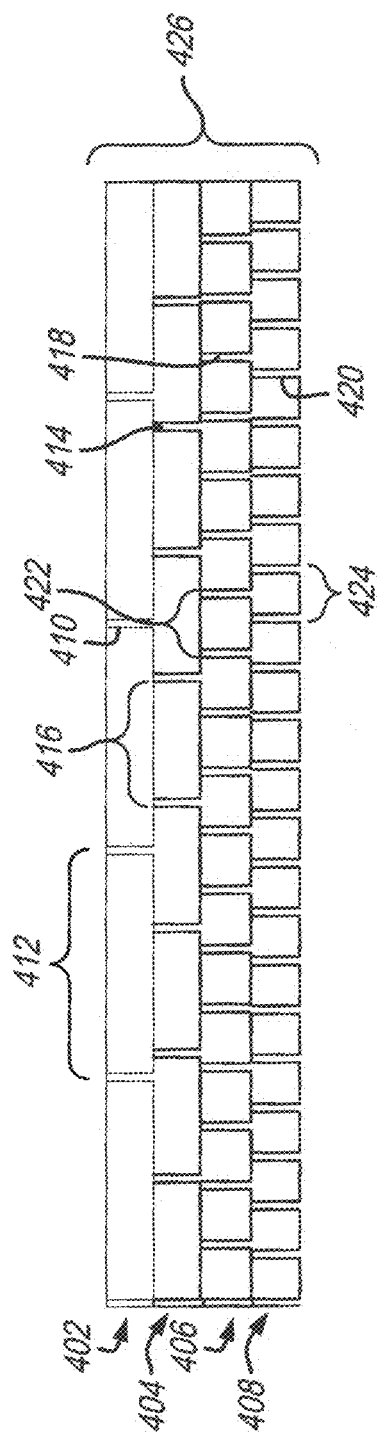
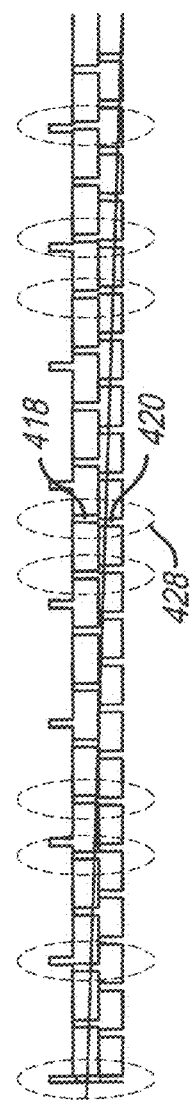
FIG. 4A
FIG. 4B

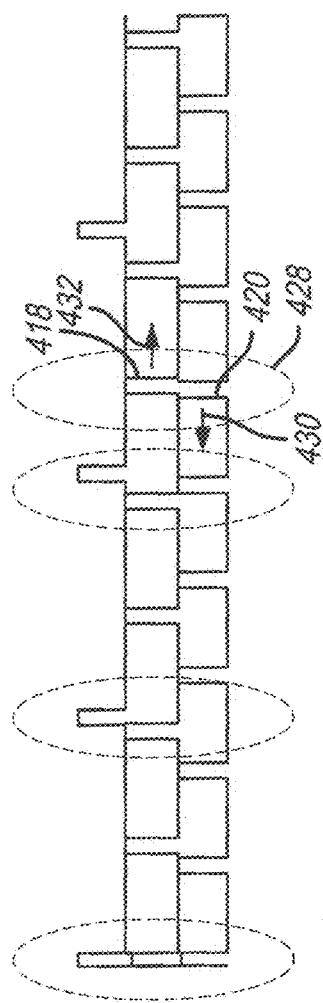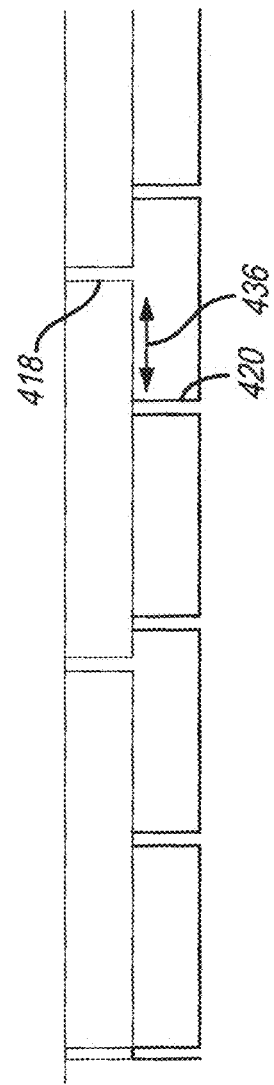

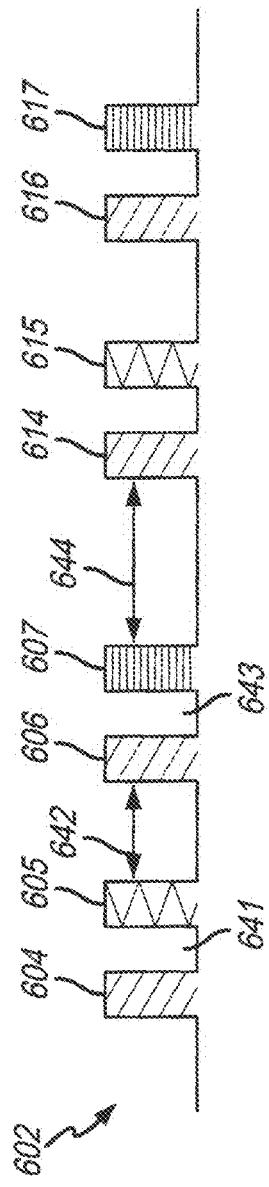
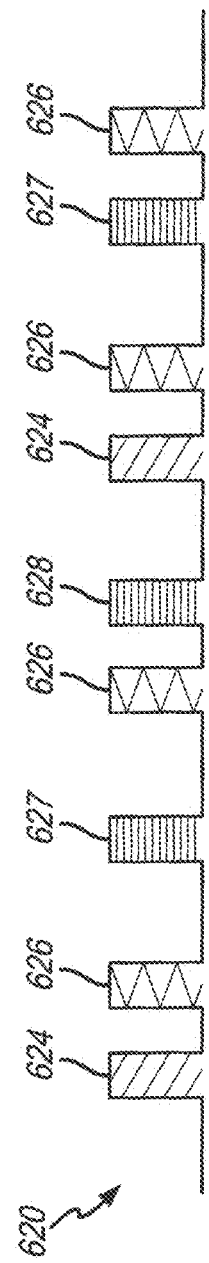
FIG. 6A
FIG. 6B

SYSTEM AND METHOD FOR INTERLEAVED NEUROSTIMULATION

BACKGROUND OF THE INVENTION

Embodiments of the present disclosure generally relate to neurostimulation (NS), and more particularly to delivering interleaved neurostimulation of multiple therapies.

NS systems are devices that generate electrical pulses and deliver the pulses to nervous tissue to treat a variety of disorders. For example, spinal cord stimulation has been used to treat chronic and intractable pain. Another example is deep brain stimulation, which has been used to treat movement disorders such as Parkinson's disease and affective disorders such as depression. SCS therapy, delivered via epidurally implanted electrodes, is a widely used treatment for chronic intractable neuropathic pain of different origins. Another stimulation configuration include burst stimulation in which sets of pulses are closely spaced.

More recently, NS systems have been developed that deliver separate stimulation therapies to nervous tissue of interest associated with separate and distinct regions of the body (also referred to as dual therapy neural stimulation systems). The NS systems utilize a lead having one or more arrays of electrodes provided thereon. One combination of electrodes is utilized to deliver a first stimulation therapy intended to act upon a first region of nervous tissue to cause a desired effect at a first body region. The same or a different combination of electrodes is utilized to deliver a second stimulation therapy configured to act upon a second region and nervous tissue to cause a desired effect at a second body region.

However, conventional neural stimulation systems exhibit limitations. For example, existing dual therapy neural stimulation systems require a separate pulse generating circuit to be utilized in connection with each stimulation therapy. Therefore, in a system designed to provide to stimulation therapies to two discrete body regions, the neural stimulation system must include two separate pulse generating circuits, along with the associated supporting electronics. Similarly, systems designed to provide more than two stimulation therapies must include a corresponding number of pulse generating circuits. With each additional pulse generating circuit, the neural stimulation system becomes larger in size and demands more power, thereby exhibiting a shorter battery life.

A need remains for methods for methods and systems that delivers multiple stimulation therapies from a common pulse generating circuit, as well as methods and systems that are able to calculate a composite pulse sequence to be generated by a common pulse generating circuit, where the composite pulse sequence is able to target multiple regions of nerve tissue of interest.

SUMMARY

In accordance with embodiments herein, a system is provided to deliver interleaved stimulation to nerve tissue of interest. The system comprises an array of stimulation electrodes. The array is configured to be implanted proximate to nerve tissue of interest. An implantable medical device (IMD) is coupled to the array. The IMD includes memory storing a composite resultant pulse (CRP) sequence comprising first and second component sequences of first and second resultant pulse trains, respectively. One or more pulses from at least one of the first or second component sequences are temporally shifted relative to a corresponding target component sequence. The IMD further comprises a pulse generating circuit and switching circuit coupled to an output of the pulse generating circuit and the array. The switching circuit is configured to connect the pulse generating circuit to different combinations of the electrodes. The IMD further comprises a processor, configured to execute program instructions stored in the memory, directs the pulse generating circuit to generate the CRP sequence and manages the switching circuit to deliver the pulses of the first and second component sequences, in an interleaved manner, to first and second electrode combinations, respectively.

Optionally, the processor may be configured to manage delivery of the first resultant pulse train to the first electrode combination, wherein pulses within the first resultant pulse train are spaced apart from one another by an uneven pulse-to-pulse interval. The uneven pulse-to-pulse interval may be within a select tolerance of an even pulse-to-pulse interval corresponding to a target pulse frequency of the corresponding target component sequence. The first resultant pulse train may include the one or more pulses that may be temporally shifted to define a pseudo frequency that may differ from a target pulse frequency of the corresponding target component sequence.

Optionally, the pseudo frequency may be within a select limit of the target pulse frequency. The pseudo frequency may include an uneven pulse-to-pulse interval between successive pulses in the first resultant pulse train. The processor may be configured to direct the switching circuit to direct first and third pulses in the CPR sequence to the first electrode combination and to direct second and fourth pulses in the CPR sequence to the second electrode combination. The CRP sequence may have a finite sequence that may be repeated by the pulse generating circuit.

In accordance with embodiments herein a method is provided to deliver interleaved stimulation to nerve tissue of interest. The method comprises providing an array of stimulation electrodes to be implanted proximate to nerve tissue of interest. The method further stores, in memory of an IMD coupled to the array, a composite resultant pulse (CRP) sequence comprising first and second component sequences of first and second resultant pulse trains, respectively. One or more pulses from at least one of the first or second component sequences are temporally shifted from a corresponding target component sequence. The method directs a pulse generating circuit, in the IMD, to generate the CRP sequence and connects an output of the pulse generating circuit to different electrode combinations to deliver the pulses of the first and second component sequences, in an interleaved manner, to the first and second electrode combinations, respectively.

Optionally, the connecting operation may manage delivery of the first resultant pulse train to the first electrode combination. Pulses within the first resultant pulse train may be spaced apart from one another by an uneven pulse-to-pulse interval. The directing operation may include maintaining the uneven pulse-to-pulse interval within a select tolerance of an even pulse-to-pulse interval corresponding to a target pulse frequency of the corresponding target component sequence. The first resultant pulse train may include the one or more pulses that may be temporally shifted to define a pseudo frequency that differs from a target pulse frequency of the corresponding target component sequence.

Optionally, the pseudo frequency may be within a select limit of the target pulse frequency. The pseudo frequency may include an uneven pulse-to-pulse interval between successive pulses in the first resultant pulse train. The connecting operation may include managing a switching circuit to direct first and third pulses in the CRP sequence to the first electrode combination and to direct second and fourth pulses in the CRP sequence to the second electrode combination. The first and second component sequences may be defined to target corresponding different first and second nerve tissue of interest.

In accordance with embodiments herein a computer implemented method provides a therapy for stimulating nerve tissue of interest. The method comprises utilizing one or more processors. The method further comprises executing program instructions stored in memory to receive characteristics that define first and second target component sequences of first and second target pulse trains. The method aligns the first and second target pulse trains along a common timeline associated with an overall sequence length to collectively define a target composite therapy. The method identifies a conflict region in which pulses in the first and second target pulse trains overlap one another in time on the timeline. The method temporally shifts one or more of the pulses in the conflict region along the timeline to form a composite resultant pulse (CRP) sequence that includes first and second component sequences of first and second resultant pulse trains, wherein one or more pulses from at least one of the first or second component sequences are temporally shifted from the corresponding first or second target component sequence.

Optionally, the method may further comprise calculating first and second types of pulse-to-pulse relative factors. The pulse-to-pulse relative factors may represent an elastic force and a repelling force. The temporal shift may be based on the pulse-to-pulse relative factors. The method may further comprise calculating an elastic force between a current pulse and one or more surrounding pulses in the first component sequence. The elastic force may represent a factor to maintain pulses of the first component sequence in a substantially even pulse-to-pulse spacing. The temporal shift may comprise shifting the current pulse based on the elastic force. The method may calculate a repelling force between a current pulse in the first component sequence and one or more pulses in the second component sequence. The repelling force may represent a factor to separate a pulse of the first component sequence from one or more surrounding pulses of the second component sequence.

BRIEF DESCRIPTION OF THE DRAWINGS

FIG. 4A illustrates a collection of pulse trains that are defined by corresponding sets of characteristics in accordance with embodiments herein.

FIG. 4B illustrates a collection of pulse trains that are defined by corresponding sets of characteristics in accordance with embodiments herein.

FIG. 4C illustrates a collection of pulse trains that are defined by corresponding sets of characteristics in accordance with embodiments herein.

FIG. 4D illustrates a collection of pulse trains that are defined by corresponding sets of characteristics in accordance with embodiments herein.

FIG. 6A illustrates a portion of a composite resultant pulse sequence that may be produced by a pulse generating circuit in accordance with embodiments herein.

FIG. 6B illustrates a portion of a CRP sequence that includes first through fourth resultant pulse trains that have been shifted to avoid temporal overlap in accordance with embodiments herein.

DETAILED DESCRIPTION

Figure 1A:
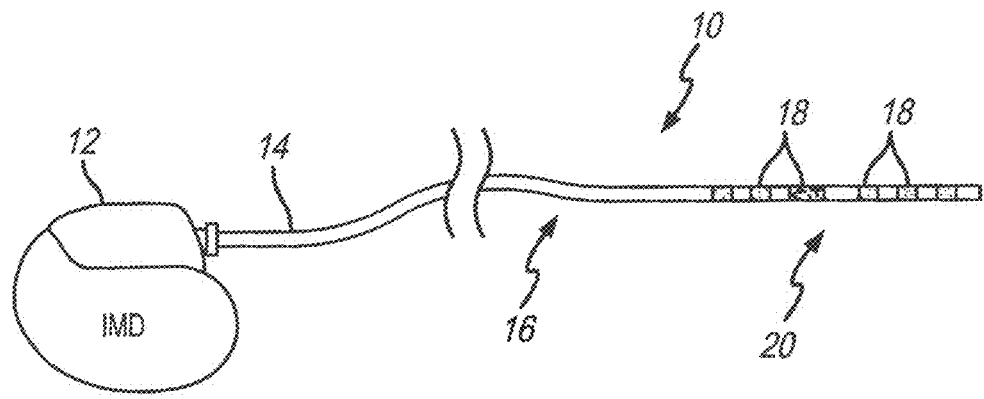
FIG. 1A illustrates an example neurological stimulation (NS) system formed in accordance with embodiments herein.

While multiple embodiments are described, still other embodiments of the described subject matter will become apparent to those skilled in the art from the following detailed description and drawings, which show and describe illustrative embodiments of disclosed inventive subject matter. As will be realized, the inventive subject matter is capable of modifications in various aspects, all without departing from the spirit and scope of the described subject matter. Accordingly, the drawings and detailed description are to be regarded as illustrative in nature and not restrictive.

I. DEFINITIONS

Unless defined otherwise, technical and scientific terms used herein have the same meaning as commonly understood by one of ordinary skill in the art to which this invention belongs. For purposes of the description, the following terms are defined below. Further, additional terms are used herein that shall have definitions consistent with the definitions set forth in U.S. Pat. No. 8,401,655, which is expressly incorporated herein by reference in its entirety.

As used herein, the use of the word "a" or "an" when used in conjunction with the term "comprising" in the claims and/or the specification may mean "one," but it is also consistent with the meaning of "one or more," "at least one," and "one or more than one." Still further, the terms "having", "including", "containing" and "comprising" are interchangeable and one of skill in the art is cognizant that these terms are open ended terms.

As used herein, the terms "burst firing", "burst type" or "burst mode" refer to an action potential that is a burst of high frequency spikes/pulses (e.g. 400-1000 Hz) (Beurrier et al., 1999). Burst firing acts in a non-linear fashion with a summation effect of each spike/pulse.

As used herein, the terms "tonic firing", "tonic type" or "tonic mode" refers to an action potential that occurs in a linear fashion.

As used herein, the term "burst" refers to a period in a pulse train that has a much higher discharge rate than surrounding periods in the pulse train (N. Urbain et al., 2002). Thus, burst can refer to a plurality of groups of pulse pulses. A burst is a train of action potentials that, possibly, occurs during a 'plateau' or 'active phase', followed by a period of relative quiescence called the 'silent phase' (Nunernaker, Celiscience Reviews Vol 2 No. 1, 2005.) Thus, a burst comprises pulses having an inter-pulse interval in which the pulses are separated by 0.5 milliseconds to about 100 milliseconds. The inter-pulse interval can be longer or shorter. Yet further, the pulse rate within the burst does not necessarily occur at a fixed rate; this rate can be variable.

The terms "pulse" and "spike" are used interchangeably to refer to an action potential.

Different firing modes or frequencies of neural oscillations occur in the brain and/or other neuronal tissue, for example tonic firing and burst firing (irregular or regular burst firing). The thalamus utilizes both types of firing modes. The two thalami (bilateral paired structures) are the gateways to the cerebral cortex and, thus, to consciousness. The thalamic nuclei specialize in several different signaling functions: transmitting signals from sensory input to the cortex; transmitting signals from cortical motor centers to effectors; transmitting control signals that select which input and output will be permitted to pass to and from the cortex and how the signals will be sequenced (thalamic reticular nuclei (TRN)); and modulating (controlling intensity) and synchronizing (grouping) the signals (Intralaminar Nuclei (ILN)).

Electrical Stimulation Devices

Figure 1B:
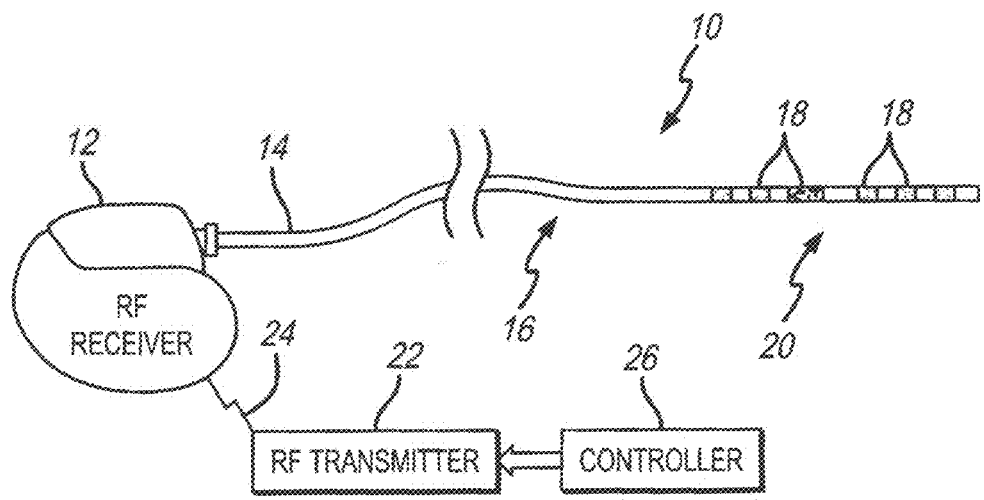
FIG. 1B illustrates an example neurological stimulation (NS) systems formed in accordance with embodiments herein.

FIGS. 1A-1B illustrate example neurological stimulation (NS) systems 10 for electrically stimulating a predetermined site area to treat one or more neurological disorders or conditions. In general terms, stimulation system 10 includes an implantable pulse generating source or electrical IMD 12 (generally referred to as an "implantable medical device" or "IMD") and one or more implantable electrodes or electrical stimulation leads 14 for applying interleaved stimulation pulses to a predetermined site. In operation, both of these primary components are implanted in the person's body, as discussed below. In certain embodiments, IMD 12 is coupled directly to a connecting portion 16 of stimulation lead 14. In other embodiments, IMD 12 is incorporated into the stimulation lead 14 and IMD 12 instead is embedded within stimulation lead 14. For example, such a stimulation system 10 may be a Bion® stimulation system manufactured by Advanced Bionics Corporation. Whether IMD 12 is coupled directly to or embedded within the stimulation lead 14, IMD 12 controls the stimulation pulses transmitted to one or more stimulation electrodes 18 located on a stimulating portion 20 of stimulation lead 14, positioned in communication with a predetermined site, according to suitable therapy parameters (e.g., duration, amplitude or intensity, frequency, pulse width, firing delay, etc.).

As contemplated in embodiments herein, a predetermined stimulation site for tissue of interest can include either peripheral neuronal tissue and/or central neuronal tissue. Neuronal tissue includes any tissue associated with the peripheral nervous system or the central nervous system. Peripheral neuronal tissue can include a nerve root or root ganglion or any neuronal tissue that lies outside the brain, brainstem or spinal cord. Peripheral nerves can include, but are not limited to olfactory nerve, optic, nerve, oculomotor nerve, trochlear nerve, trigeminal nerve, abducens nerve, facial nerve, vestibulocochlear (auditory) nerve, glossopharyngeal nerve, vagal nerve, accessory nerve, hypoglossal nerve, suboccipital nerve, the greater occipital nerve, the lesser occipital nerve, the greater auricular nerve, the lesser auricular nerve, the phrenic nerve, brachial plexus, radial axillary nerves, musculocutaneous nerves, radial nerves, ulnar nerves, median nerves, intercostal nerves, lumbosacral plexus, sciatic nerves, common peroneal nerve, tibial nerves, sural nerves, femoral nerves, gluteal nerves, thoracic spinal nerves, obturator nerves, digital nerves, pudendal nerves, plantar nerves, saphenous nerves, ilioinguinal nerves, gentofemoral nerves, and iliohypogastric nerves.

Central neuronal tissue includes brain tissue, spinal tissue or brainstem tissue. Brain tissue can include thalamus/subthalamus, basal ganglia, hippocampus, amygdala, hypothalamus, mammilary bodies, substantia nigra or cortex or white matter tracts afferent to or efferent from the above-mentioned brain tissue, inclusive of the corpus callosum. Spinal tissue can include the ascending and descending tracts of the spinal cord, more specifically, the ascending tracts of that comprise intralaminar neurons or the dorsal column. The brainstem tissue can include the medulla oblongata, pons or mesencephalon, more particular the posterior pons or posterior mesencephalon, Lushka's foramen, and ventrolateral part of the medulla oblongata.

In FIG. 1B, the IMD 12 includes an implantable wireless receiver. An example of a wireless receiver may be one manufactured by Advanced Neuromodulation Systems, Inc., such as the Renew® system, part numbers 3408 and 3416. The wireless receiver is capable of receiving wireless signals from a wireless transmitter 22 located external to the person's body. The wireless signals are represented in FIG. 1B by wireless link symbol 24. A doctor, the patient, or another user of IMD 12 may use a controller 26 located external to the person's body to provide control signals for operation of IM D 12. Controller 26 provides the control signals to wireless transmitter 22, wireless transmitter 22 transmits the control signals and power to the wireless receiver of IMD 12, and IMD 12 uses the control signals to vary the signal parameters of electrical signals transmitted through electrical stimulation lead 14 to the stimulation site. Thus, the external controller 26 can be for example, a handheld programmer, to provide a means for programming the IMD. An example wireless transmitter may be one manufactured by Advanced Neuromodulation Systems, Inc., such as the Renew® system, part numbers 3508 and 3516.

The IMD 12 includes a microprocessor and a pulse generation module. The pulse generation module generates the electrical pulses according to a defined pulse width, pulse amplitude and pulse-to-pulse interval, and applies the electrical pulses to defined electrodes (or electrode combinations). The microprocessor controls the operations of the pulse generation module according to program instructions stored in memory in the IMD 12.

The IMD 12 can be adapted by programming the microprocessor to deliver a number of pulses that are separated by an appropriate pulse-to-pulse interval. Optionally, when utilizing burst stimulation, the programming of the microprocessor may cause the pulse generation module to cease pulse generation operations for an interburst interval.

The microprocessor can be programmed to allow the various characteristics of the therapy to be set automatically or by a physician to allow the pulse trains to be customized for multiple particular pathologies of a patient. For example, the pulse amplitude, the interpulse interval, the interburst interval, the number of bursts to be repeated in succession, the electrode combinations, the firing delay between interleaved stimulation waveforms delivered to different electrode combinations, the amplitude of the hyperpolarizing pulse, and other such characteristics could be controlled using respective parameters accessed by the microprocessor during burst stimulus operations. These parameters could be set to desired values by an external programming device via implementing the processes described herein to form a CRP sequence. The CRP sequence is transmitted wireless communication to the implantable neuromodulation device.

In another embodiment, the IMD 12 can be implemented to apply the CRP sequence using a digital signal processor and one or several digital-to-analog converters. The stimulus waveform could be defined in memory and applied to a pulse generating circuit for application through electrodes of the medical lead. The digital signal processor could scale the various portions of the waveform output by the pulse generating circuit in amplitude and within the time domain (e.g., for the various intervals) according to the various parameters.

Figure 1C:
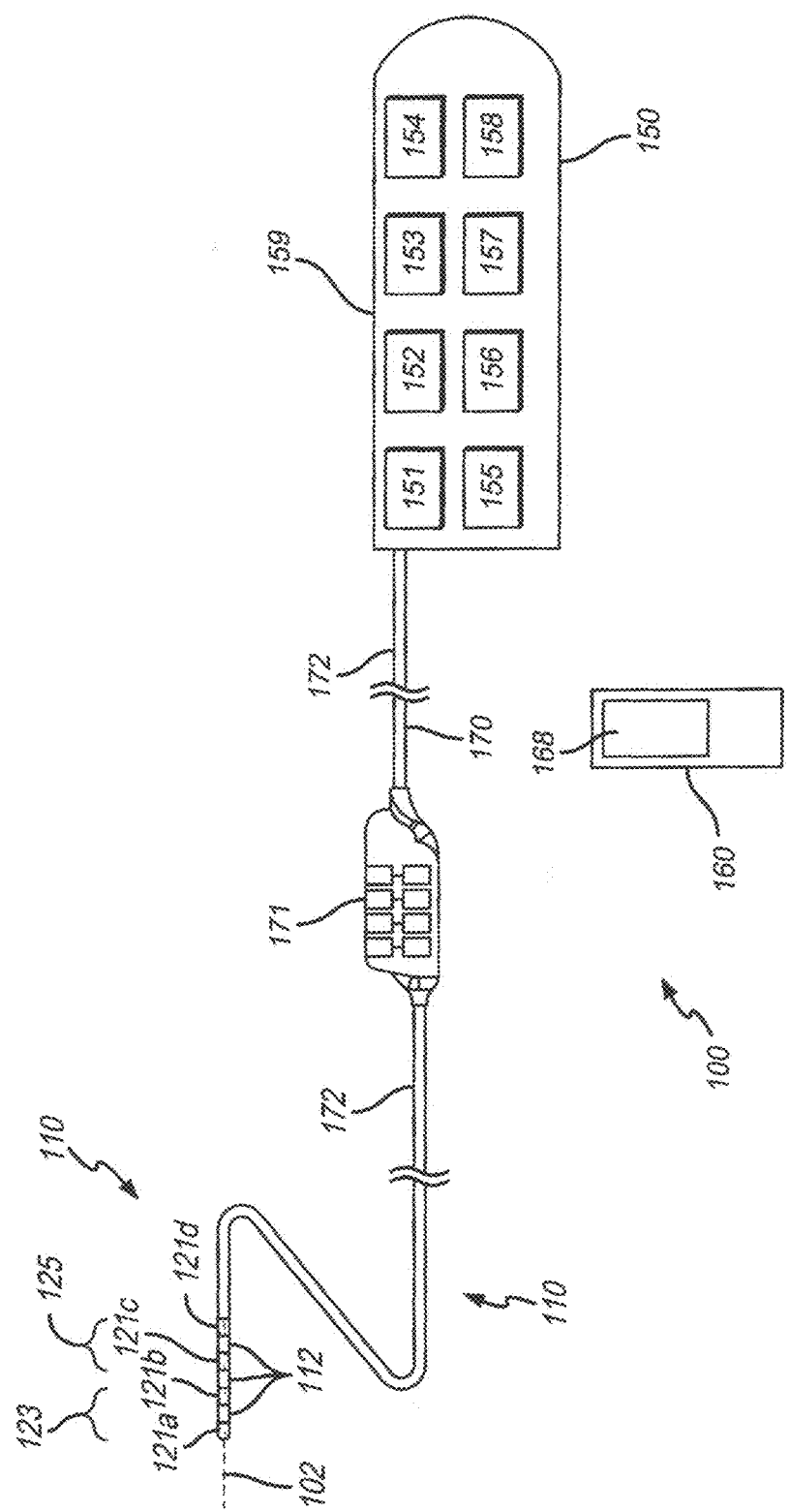
FIG. 1C depicts an NS system that delivers interleaved therapies in accordance with embodiments herein.
Figure 2A:
FIG. 2A illustrates example stimulation leads that may be used for electrically stimulating the predetermined site in accordance with embodiments herein.
Figure 2B:
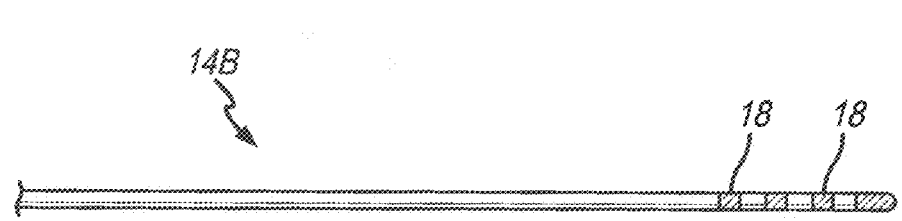
FIG. 2B illustrates example stimulation leads that may be used for electrically stimulating the predetermined site in accordance with embodiments herein.
Figure 2C:
FIG. 2C illustrates example stimulation leads that may be used for electrically stimulating the predetermined site in accordance with embodiments herein.
Figure 2D:
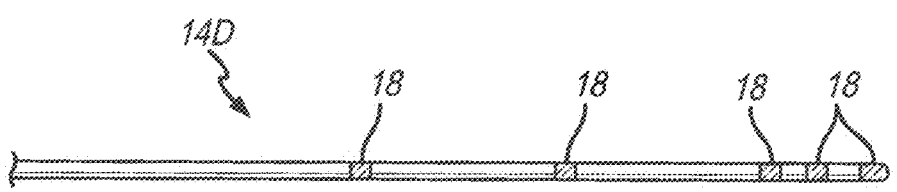
FIG. 2D illustrates example stimulation leads that may be used for electrically stimulating the predetermined site in accordance with embodiments herein.
Figure 2E:
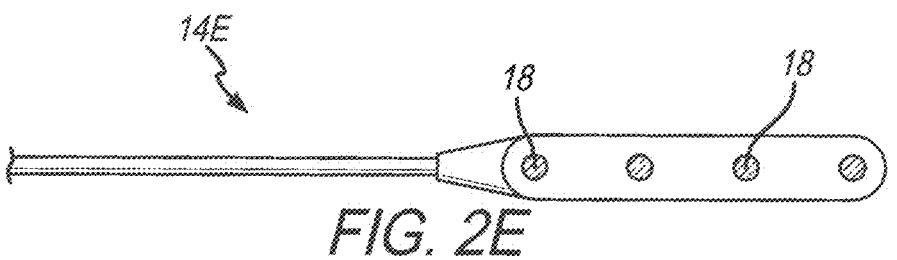
FIG. 2E illustrates example stimulation leads that may be used for electrically stimulating the predetermined site in accordance with embodiments herein.
Figure 2F:
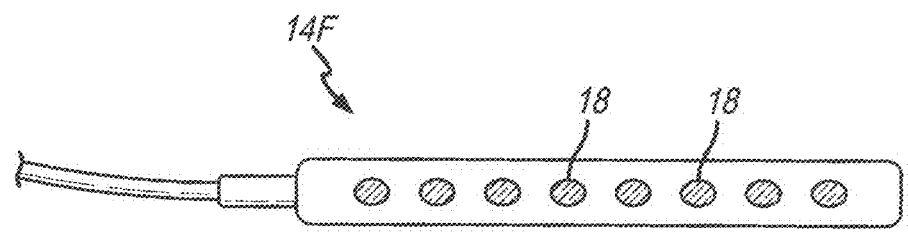
FIG. 2F illustrates example stimulation leads that may be used for electrically stimulating the predetermined site in accordance with embodiments herein.
Figure 2G:
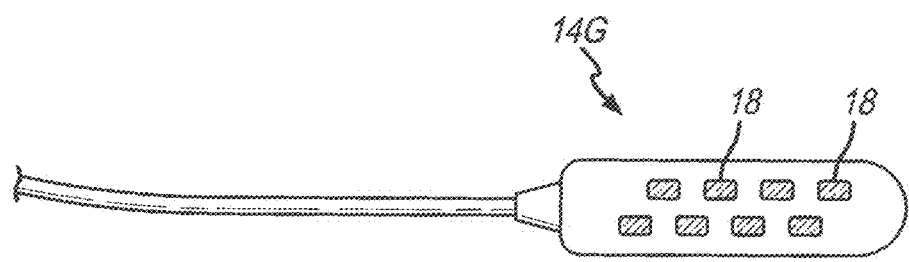
FIG. 2G illustrates example stimulation leads that may be used for electrically stimulating the predetermined site in accordance with embodiments herein.
Figure 2H:
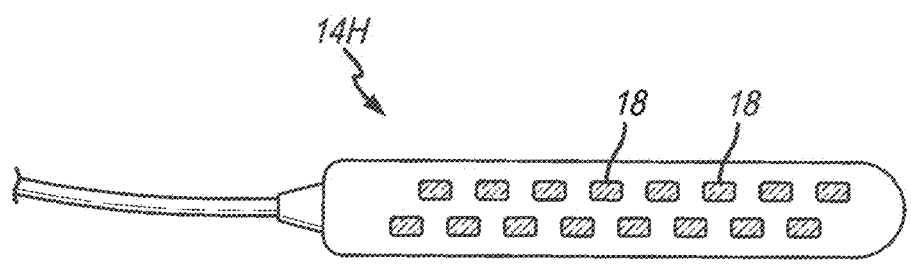
FIG. 2H illustrates example stimulation leads that may be used for electrically stimulating the predetermined site in accordance with embodiments herein.
Figure 2I:
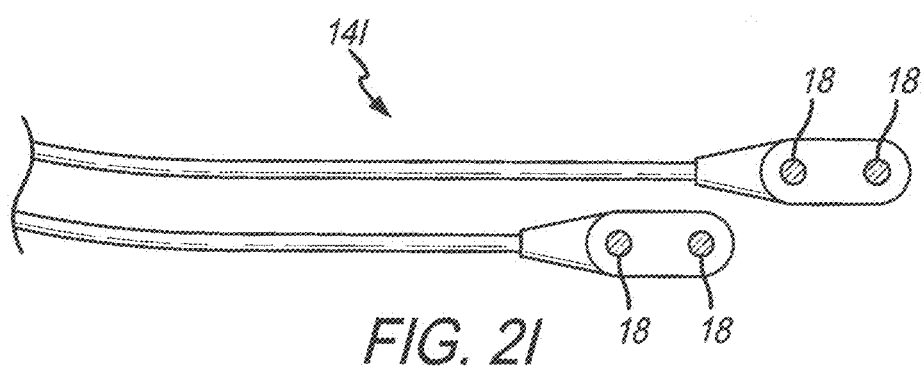
FIG. 2I illustrates example stimulation leads that may be used for electrically stimulating the predetermined site in accordance with embodiments herein.

FIG. 1C depicts an NS system 100 that delivers interleaved therapies targeted to multiple patient body parts (through corresponding portions of the nerve tissue). For example, the NS system 100 may be adapted to stimulate spinal cord tissue, peripheral nervous tissue, deep brain tissue, and/or any other suitable nervous/brain tissue of interest within a patient's body.

The NS system 100 may be controlled to deliver various types of interleaved stimulation therapy, such as multiple different tonic neurostimulation therapies, burst neurostimulation therapies and combinations thereof. Burst neurostimulation includes short sequences of monophasic or biphasic pulses, where each sequence is separated by a quiescent period.

The NS system 100 delivers interleaved stimulation therapy based on a preprogrammed CRP sequence. The therapy parameters of the CRP sequence may include, among other things, pulse amplitude, pulse polarity, pulse width, pulse frequency, interpulse interval, inter burst interval, electrode combinations, firing delay and the like. Optionally, the NS system 100 may represent a closed loop neurostimulation device that is configured to provide real-time sensing functions from a lead. The configuration of the lead sensing electrodes may be varied depending on the neuronal anatomy of the sensing site(s) of interest. The size and shape of electrodes is varied based on the implant location. The electronic components within the NS system 100 are designed with both stimulation and sensing capabilities, including alternative interleaved stimulation therapy, such as burst mode and the like.

The NS system 100 includes an implantable medical device (IMD) 150 that is adapted to generate electrical pulses for application to tissue of a patient. The IMD 150 typically comprises a metallic housing or can 158 that encloses a controller 151, pulse generating circuit 152, a charge storage circuit 153, a battery 154, a far-field and/or near field communication circuit 155, battery charging circuit 156, switching circuit 157, memory 158 and the like. The charge storage circuit 153 may represent one or more capacitors and/or battery cells that store charge used to produce the therapies described herein. The pulse generating circuit 152, under control of control of the controller 151, manages discharge of the charge storage circuit 153 to generate the CRP sequence (shape the morphology of the waveform) delivered while discharging energy. The switching circuit 157 connects select combinations of the electrodes 121*a*-*d* to the pulse generating circuit 152 thereby directing the stimulation waveform to a desired electrode combination. By way of example, the switching circuit 157 may include one or more multiplexer circuits connected between the output of the pulse generating circuit and the electrodes. As explained herein, the switching circuit 157 successively connects the pulse generating circuit 152 to successive electrode combinations 123 and 125. The components 151-158 are also within the IMD 12 (FIGS. 1A and 1B).

The controller 151 typically includes one or more processors, such as a microcontroller, for controlling the various other components of the device. Software code is typically stored in memory of the IMD 150 for execution by the microcontroller or processor to control the various components of the device.

The IMD 150 may comprise a separate or an attached extension component 170. If the extension component 170 is a separate component, the extension component 170 may connect with the "header" portion of the IMD 150 as is known in the art. If the extension component 170 is integrated with the IMD 150, internal electrical connections may be made through respective conductive components. Within the IMD 150, electrical pulses are generated by the pulse generating circuit 152 and are provided to the switching circuit 157. The switching circuit 157 connects to outputs of the IMD 150. Electrical connectors (e.g., "Bal-Seal" connectors) within the connector portion 171 of the extension component 170 or within the IMD header may be employed to conduct various stimulation pulses. The terminals of one or more leads 110 are inserted within connector portion 171 or within the IMD header for electrical connection with respective connectors. Thereby, the pulses originating from the IMD 150 are provided to the lead 110. The pulses are then conducted through the conductors of the lead 110 and applied to tissue of a patient via stimulation electrodes 121*a-d* that are coupled to blocking capacitors. Any suitable known or later developed design may be employed for connector portion 171.

The stimulation electrodes 121*a-d* may be positioned along a horizontal axis 102 of the lead 110, and are angularly positioned about the horizontal axis 102 so the stimulation electrodes 121*a-d* do not overlap. The stimulation electrodes 121*a-d* may be in the shape of a ring such that each stimulation electrode 121*a-d* continuously covers the circumference of the exterior surface of the lead 110. Adjacent stimulation electrodes 121*a-d* are separated from one another by non-conducting rings 112, which electrically isolate each stimulation electrode 121*a-d* from an adjacent stimulation electrode 121*a-d*. The non-conducting rings 112 may include one or more insulative materials and/or biocompatible materials to allow the lead 110 to be implantable within the patient. Non-limiting examples of such materials include polyimide, polyetheretherketone (PEEK), polyethylene terephthalate (PET) film (also known as polyester or Mylar), polytetrafluoroethylene (PTFE) (e.g., Teflon), or parylene coating, polyether bloc amides, polyurethane. The stimulation electrodes 121*a-d* may be configured to emit the pulses in an outward radial direction proximate to or within a stimulation target. Additionally or alternatively, the stimulation electrodes 121*a-d* may be in the shape of a split or non-continuous ring such that the pulse may be directed in an outward radial direction adjacent to the stimulation electrodes 121*a-d*. The stimulation electrodes 121*a-d* deliver tonic, and/or burst interleaved stimulation waveforms as described herein. Optionally, the electrodes 121*a-d* may also sense neural oscillations and/or sensory action potential (neural oscillation signals) for a data collection window.

The lead 110 may comprise a lead body 172 of insulative material about a plurality of conductors within the material that extend from a proximal end of lead 110, proximate to the IMD 150, to its distal end. The conductors electrically couple a plurality of the stimulation electrodes 121 to a plurality of terminals (not shown) of the lead 110. The terminals are adapted to receive electrical pulses and the stimulation electrodes 121*a-d* are adapted to apply the pulses to the stimulation target of the patient. Also, sensing of physiological signals may occur through the stimulation electrodes 121*a-d*, the conductors, and the terminals. It should be noted that although the lead 110 is depicted with four stimulation electrodes 121*a-d*, the lead 110 may include any suitable number of stimulation electrodes 121*a-d* (e.g., less than four, more than four) as well as terminals, and internal conductors. Additionally or alternatively, various sensors (e.g., a position detector, a radiopaque fiducial) may be located near the distal end of the lead 110 and electrically coupled to terminals through conductors within the lead body 172.

Although not required for any embodiments, the lead body 172 of the lead 110 may be fabricated to flex and elongate upon implantation or advancing within the tissue (e.g., nervous tissue) of the patient towards the stimulation target and movements of the patient during or after implantation. By fabricating the lead body 172, according to some embodiments, the lead body 172 or a portion thereof is capable of elastic elongation under relatively low stretching forces. Also, after removal of the stretching force, the lead body 172 may be capable of resuming its original length and profile.

By way of example, the IMD 12, 150 may include a processor and associated charge control circuit as described in U.S. Pat. No. 7,571,007, entitled "SYSTEMS AND METHODS FOR USE IN PULSE GENERATION," which is expressly incorporated herein by reference. Circuit for recharging a rechargeable battery (e.g., battery charging circuit 156) of an IMD using inductive coupling and external charging circuits are described in U.S. Pat. No. 7,212,110, entitled "IMPLANTABLE DEVICE AND SYSTEM FOR WIRELESS COMMUNICATION," which is expressly incorporated herein by reference. An example and discussion of "constant current" pulse generating circuit (e.g., pulse generating circuit 152) is provided in U.S. Patent Publication No. 2006/0170486 entitled "PULSE GENERATOR HAVING AN EFFICIENT FRACTIONAL VOLTAGE CONVERTER AND METHOD OF USE," which is expressly incorporated herein by reference. One or multiple sets of such circuit may be provided within the IMD 12, 150. Different burst and/or tonic pulses on different stimulation electrodes may be generated using a single pulse generating circuit using consecutively generated pulses. Complex pulse parameters may be employed such as those described in U.S. Pat. No. 7,228,179, entitled "Method and apparatus for providing complex tissue stimulation patterns," and International Patent Publication Number WO 2001/093953 A1, entitled "NEUROMODULATION THERAPY SYSTEM," which are expressly incorporated herein by reference. Alternatively, multiple sets of pulse generating circuit may be employed to provide a greater number of component sequences (e.g., one PG to produce two tonic stimulation waveforms and one PG to produce a burst stimulation waveform) that include generated and delivered stimulation pulses through various stimulation electrodes of one or more leads. Although constant current pulse generating circuit is contemplated for some embodiments, any other suitable type of pulse generating circuit may be employed such as constant voltage pulse generating circuit.

The controller 151 delivers the interleaved stimulation waveform (corresponding to the corrected CRP sequence) to at least two electrode combinations located proximate to nervous tissue of interest. As explained herein, one or more processors of the IMD operate by executing the following operations in a loop: set the switching/multiplexer circuit (MUX) address=n, where address n directs a current pulse to a select electrode location n (or electrode combination n); direct the pulse generating circuit to produce a pulse of width PWn; and wait a predetermined period of time corresponding to an interpulse delay tn before repeating the operations. When delivering multiple therapies from one corrected CRP sequence (e.g., designated for different body parts), it is desirable to arrange the pulses in such a way, that each electrode combination or nerve tissue location of interest receives pulses at the desired "resultant pseudo" frequency. An additional goal is to have some time interval (an inter-pulse delay) between consecutive pulses in the final or corrected CRP sequence, where the time interval is predetermined in order to allow for discharge of the output capacitors of the pulse generating circuit between pulses.

Memory 158 stores software to control operation of the controller 151 for interleaved component sequences into the final CRP sequence as explained herein. The memory 158 also stores neural oscillation signals, therapy parameters, neural oscillation activity level data, sensation scales and the like. For example, the memory 158 may save neural oscillation activity level data for various different therapies as applied over a short or extended period of time. A collection of neural oscillation activity level data is accumulated for different therapies and may be compared to identify high, low and acceptable amounts of sensory activity.

An external device 160 may be implemented to charge/recharge the battery 154 of the IMD 150 (although a separate recharging device could alternatively be employed) and to program the IMD 150 on the pulse specifications while implanted within the patient. The external device 160 may represent physician programmer device, a personal computer, workstation, server, laptop computer, table device, smart phone and the like. Although, in alternative embodiments separate programmer devices may be employed for charging and/or programming the NS system 100. The external device 160 may be a processor-based system that possesses wireless communication capabilities. Software may be stored within a non-transitory memory of the external device 160, which may be executed by the processor to control the various operations of the external device 160. The external device 160 communicates with the IMD 150 utilizing a wireless communications protocol, such as the Bluetooth protocol and the like.

Alternatively or additionally, a "wand" (not shown) may be electrically connected to the external device 160 through suitable electrical connectors (not shown). The wand may include a telemetry component (e.g., inductor coil, RF transceiver) (not shown) that allows bi-directional communication with the IMD 150.

The external device 160 preferably provides one or more user interfaces 168 (e.g., touchscreen, keyboard, mouse, buttons, or the like) allowing the user to operate the IMD 150. The external device 160 may be controlled by the user (e.g., doctor, clinician) through the user interface 168 allowing the user to interact with the IMD 150. The user interface 168 may permit the user to move electrical stimulation along and/or across one or more of the lead(s) 110 using different stimulation electrode 121 combinations, for example, as described in U.S. Patent Application Publication No. 2009/0326608, entitled "METHOD OF ELECTRICALLY STIMULATING TISSUE OF A PATIENT BY SHIFTING A LOCUS OF STIMULATION AND SYSTEM EMPLOYING THE SAME," which is expressly incorporated herein by reference.

Also, the external device 160 may permit operation of the IMD 12, 150 by loading one or more therapies (CRP sequences) to treat the patient. Each CRP sequence includes one or more sets of stimulation parameters, including pulse amplitude, pulse width, pulse frequency or inter-pulse period, firing delay, pulse repetition parameter (e.g., number of times for a given pulse to be repeated for respective stimset during execution of program), biphasic pulses, monophasic pulses, etc. The IMD 150 modifies its internal parameters in response to the control signals from the external device 160 to vary the stimulation characteristics of the stimulation pulses transmitted through the lead 110 to the tissue of the patient. NS systems, stimsets, and multi-stimset programs are discussed in PCT Publication No. WO 01/93953, entitled "NEUROMODULATION THERAPY SYSTEM," and U.S. Pat. No. 7,228,179, entitled "METHOD AND APPARATUS FOR PROVIDING COMPLEX TISSUE STIMULATION PATTERNS," which are expressly incorporated herein by reference.

FIGS. 2A-2I illustrate example stimulation leads 14 that may be used for electrically stimulating the predetermined site to treat one or more neurological disorders or conditions. As described above, each of the one or more stimulation leads 14 incorporated in stimulation systems 10, 100 includes one or more stimulation electrodes 18 adapted to be positioned in communication with the predetermined site and used to deliver the stimulation pulses received from IMD 12 (or pulse generating circuit 157 in FIG. 1C). A percutaneous stimulation lead 14 (corresponding to the lead 110 in FIG. 1C), such as example stimulation leads 14a-d, includes one or more circumferential electrodes 18 spaced apart from one another along the length of stimulating portion 20 of stimulation lead 14. Circumferential electrodes 18 emit electrical stimulation energy generally radially (e.g., generally perpendicular to the axis of stimulation lead 14) in all directions. A laminoutomy, paddle, or surgical stimulation lead 14, such as example stimulation leads 14e-i, includes one or more directional stimulation electrodes 18 spaced apart from one another along one surface of stimulation lead 14. Directional stimulation electrodes 18 emit electrical stimulation energy in a direction generally perpendicular to the surface of stimulation lead 14 on which they are located. Although various types of stimulation leads 14 are shown as examples, embodiments herein contemplate stimulation system 10 including any suitable type of stimulation lead 14 in any suitable number. In addition, stimulation leads 14 may be used alone or in combination. For example, medial or unilateral stimulation of the predetermined site may be accomplished using a single electrical stimulation lead 14 implanted in communication with the predetermined site in one side of the head, while bilateral electrical stimulation of the predetermined site may be accomplished using two stimulation leads 14 implanted in communication with the predetermined site in opposite sides of the head.

In one embodiment, the stimulation source is transcutaneously in communication with the electrical stimulation lead. In "transcutaneous" electrical nerve stimulation (TENS), the stimulation source is external to the patient's body, and may be worn in an appropriate fanny pack or belt, and the electrical stimulation lead is in communication with the stimulation source, either remotely or directly. In another embodiment, the stimulation is percutaneous. In "percutaneous" electrical nerve stimulation (PENS), needles are inserted to an appropriate depth around or immediately adjacent to a predetermined stimulation site, and then stimulated.

The IMD 12, 150 allow each electrode of each lead to be defined as a positive, a negative, or a neutral polarity. For each electrode combination (e.g., the defined polarity of at least two electrodes having at least one cathode and at least one anode), an electrical signal can have at least a definable amplitude (e.g., voltage), pulse width, and frequency, where these variables may be independently adjusted to finely select the sensory transmitting brain tissue required to inhibit transmission of neuronal signals. Generally, amplitudes, pulse widths, and frequencies are determinable by the capabilities of the neurostimulation systems, which are known by those of skill in the art. Voltages that may be used can include, for example about 0.5 to about 10 volts, more preferably about 1 to about 10 volts.

In embodiments herein, the burst stimulus frequency component of a CRP sequence may be in the range of about 1 Hz to about 100 Hz, more particular, in the range of about 1 Hz to about 12 Hz, and more particularly, in the range of about 1 Hz to about 4 Hz, 4 Hz to about 7 Hz or about 8 Hz to about 12 Hz for each burst. Each burst stimulus comprises at least two pulses, for example, each burst stimulus can comprise about 2 to about 100 pulses, more particularly, about 2 to about 10 pulses. Each pulse can comprise a frequency in the range of about 50 Hz to about 1000 Hz, more particularly, in the range of about 200 Hz to about 500 Hz. The frequency for each pulse within a burst can be variable, thus it is not necessary for each pulse to contain similar frequencies, e.g., the frequencies can vary in each pulse. The inter-pulse interval can be also vary, for example, the inter-pulse interval, can be about 0.5 milliseconds to about 100 milliseconds or any range therebetween.

The burst stimulus is followed by an inter-burst interval. The inter-burst interval has duration in the range of about 5 milliseconds to about 5 seconds, more preferably, 10 milliseconds to about 300 milliseconds. It is envisioned that the burst stimulus has a duration in the range of about 10 milliseconds to about 5 seconds, more particular, in the range of about 250 msec to 1000 msec (1-4 Hz burst firing), 145 msec to about 250 msec (4-7 Hz,), 145 msec to about 80 msec (8-12 Hz) or 1 to 5 seconds in plateau potential firing. The burst stimulus and the inter-burst interval can have a regular pattern or an irregular pattern (e.g., random or irregular harmonics).

It is envisaged that the patient will require intermittent assessment with regard to patterns of stimulation. Different electrodes on the lead can be selected by suitable computer programming, such as that described in U.S. Pat. No. 5,938,690, which is incorporated by reference here in full. Utilizing such a program allows an optimal stimulation pattern to be obtained at minimal voltages. This ensures a longer battery life for the implanted systems.

FIGS. 2A-2I respectively depict stimulation portions for inclusion at the distal end of lead. Stimulation portion depicts a conventional stimulation portion of a "percutaneous" lead with multiple ring electrodes. Stimulation portion depicts a stimulation portion including several segmented electrodes. Example fabrication processes are disclosed in U.S. patent application Ser. No. 12/895,096, entitled, "METHOD OF FABRICATING STIMULATION LEAD FOR APPLYING ELECTRICAL STIMULATION TO TISSUE OF A PATIENT," which is incorporated herein by reference. Stimulation portion includes multiple planar electrodes on a paddle structure.

Methods for Delivering Composite Resultant Pulse Sequences

Figure 3:
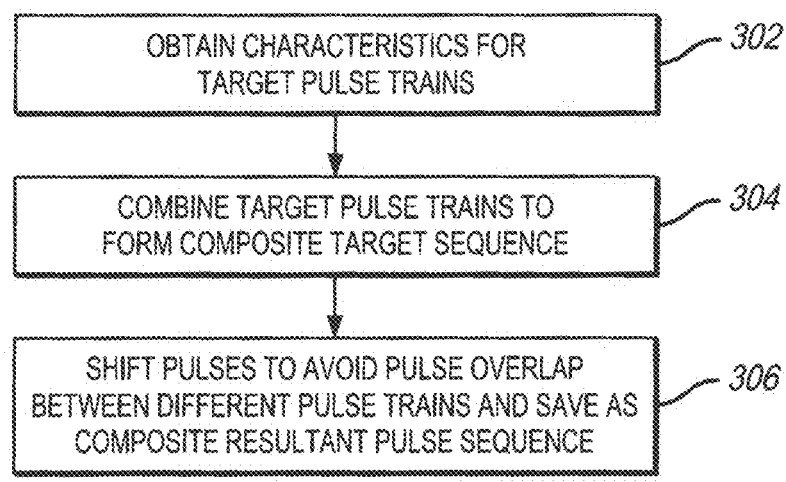
FIG. 3 illustrates a process for calculating a final or corrected composite resultant pulse (CRP) sequence in accordance with embodiments herein.

FIG. 3 illustrates a process for calculating a final or corrected composite resultant pulse (CRP) sequence in accordance with embodiments herein. The process of FIG. 3 will be described in connection with the diagrams of FIGS. 4A-4D. At 302, the processor obtains characteristics defining multiple target component sequences having corresponding target pulse trains, that are desirable to deliver to corresponding electrode combinations. Each of the target component sequences is associated with a different target therapy to be delivered to a corresponding part of the patient's nerve tissue of interest. Examples of characteristics include pulse amplitude, pulse width, electrode configuration, burst or tonic type stimulation, pulse-to-pulse interval, pulse frequency and the like. Various combinations of the characteristics represent sets of characteristics where one set of characteristics is associated with a corresponding single target component sequence and target pulse train.

FIG. 4A illustrates a collection of four target pulse trains 402-408 that are defined by corresponding sets of characteristics. Each target pulse train 402-408 corresponds to a target therapy, and is also referred to as a target component sequence. For example, the target pulse train 402 (target component sequence) includes a series of pulses 410 having a predetermined pulse amplitude and pulse width. The pulses 410 are separated by a pulse-to-pulse interval 412. By way of example, the pulse-to-pulse interval 412 may be measured between the rising edges of successive pulses 410. The pulse-to-pulse interval 412 is dependent on a target pulse frequency. In the example of FIG. 4A, the target pulse train 404 includes a series of pulses 414 that are separated by a pulse-to-pulse interval 416. Continuing with the example of FIG. 4A, the target pulse trains 406, 408 include corresponding series of pulses 418, 420. The pulses 418 are separated by pulse-to-pulse intervals 422, while the pulses 420 are separated by pulse-to-pulse intervals 424.

In a target or preferred implementation, each of the pulse trains 402-408 would be delivered (in the original form) to a corresponding electrode combination in connection with delivering a corresponding therapy targeted for a select region of the patient. In the target implementation, stimulation would be delivered to designated electrode combinations where the stimulation would have pulse width, pulse frequency, etc., matching the target pulse trains 402-408. The target pulse trains 402-408 collectively defined a target composite pulse sequence 426. While four separate pulse trains are illustrated, more or fewer pulse trains may be utilized.

The pulse train 402 may represent a tonic type stimulation that is delivered to never tissue of interest, such as designed to introduce paresthesia into the distal portion of a leg or arm. As another example, pulse train 406 may represent a burst type stimulation (where each of the pulses 418 represents a short burst of spikes) that is delivered to nerve tissue of interest designed to suppress pain, a tremor, and the like in a another anatomic region (e.g. a hand or arm). As a further example, each of the pulse trains 402-408 may represent tonic type stimulations to be delivered to nerve tissue of interest in connection with separate and distinct regions of a patient's legs, arms, torso, head and the like. One or more electrode combinations are designated to correspond to each of the target pulse trains 402-408. For example, when the electrode array is arranged in a two-dimensional array, the target pulse train 402 may be associated with an electrode combination located in one or more rows of the array. Alternatively, the target pulse train 402 may be associated with an electrode combination located in one or more columns of the array. Additionally or alternatively, the target pulse train 404 may be associated with one or more electrode combinations in a different row(s) and/or different column(s) of the array.

When the array represents a one-dimensional array of electrodes (e.g., as illustrated in FIGS. 2A-2F), first and second subsets of the electrodes may be designated for use with the target pulse trains 402 and 404, respectively. A common or a different subset of electrodes may be designated for use with target pulse trains 406 and 408. The electrode combinations designated for use with each of the target pulse trains 402-408 may be separate and distinct from one another, partially overlap or entirely overlap. For example, the target pulse trains 402-408 may be designated to be used with first through fourth electrode combinations. When using separate and distinct electrode combinations, the electrodes in the first electrode combination may not be used in any of the second through fourth electrode combinations. Similarly, the electrodes in the second electrode combination may not be used in any of the first, third or fourth electrode combinations. When using partially overlapping electrode combinations, one or more of the electrodes in the first electrode combination may be used in one or more of the second through fourth electrode combinations. Additionally or alternatively, the electrodes in the second electrode combination may be used in one or more of the first, third and fourth electrode combinations. When using entirely overlapping electrode combinations, all of the electrodes in the first electrode combination are used in one or more of the second through fourth electrode combinations. Additionally or alternatively, all of the electrodes in the second electrode combination may be used in one or more of the first, third and fourth electrode combinations.

The electrode combinations designated for use with each of the target pulse trains 402-408 may include similarly shaped and dimensioned patterns, and/or differently shaped and/or dimensioned patterns. For example, the first electrode combination may use one row or one column of electrodes, while the second electrode combination may use 2 or more rows or columns of electrodes. As another example, the third electrode combination may utilize a large two dimensional array of electrodes (e.g., 6 rows by 3 columns), while the fourth electrode combination may utilize a small two dimensional array of electrodes (e.g., 4 rows by 1 column).

Returning to FIG. 3, at 304, one or more processors combine the target pulse trains to form a composite target sequence. With reference to FIG. 4A, the target pulse trains 402-408 are combined to form a composite target sequence 426. As illustrated in FIG. 4A, individual pulses overlap at various points during the target pulse trains 402-408. Overlapping pulses represent conflict regions, as noted within the dashed ovals in FIG. 4B. In FIG. 4B, the conflict region 428 shows a pulse 420 and a pulse 418 to overlap in time when the target pulse trains 406, 408 are aligned along a common timeline associated with the composite target sequence. As explained herein, various techniques are presented to adjust the pulses to remove conflicts/overlap.

Returning to FIG. 3, at 306, one or more processors shifts one or more of the overlapping pulses in the conflict regions until overlap is avoided between the different pulse trains. Once the pulses are shifted to a non-overlap relation, the resulting combination of pulse trains represent the composite resultant pulse sequence and therapy that is saved in memory.

With reference to FIG. 4C, by way of example, in conflict region 428, the pulse 420 may be shifted in time to the left (earlier) as indicated by arrow 430. Optionally or additionally, the pulse 418 may be shifted in time to the right (lagging) as noted by arrow 432. One or both of the pulses 420, 418 may be shifted during an iterative process by small amounts until no overlap is identified. For example, the pulses 420, 418 may be shifted until offset as illustrated in FIG. 4I), until a pulse delay 436 is achieved. It is recognized that the example of FIG. 4D may represent an exaggeration of the amount of shift or pulse delay 436 introduced between successive pulses from different pulse trains. More or less shift may be introduced.

Returning to FIG. 3, more detailed examples of the operations are described herein in connection with various embodiments. The operations of FIG. 3 may be carried out by one or more processors within IMD, within an external device while communicating with an IMD, by an external device entirely independent of and separate from communication with an IMD, by a server on a hospital network, a physician's workstation, or other computing device. Additionally or alternatively, the operations of FIG. 3 may be distributed between multiple devices, such as between an IMD and an external device, an extranet device and a hospital network server, the hospital network server and a physician's workstation and the like.

Figure 5:
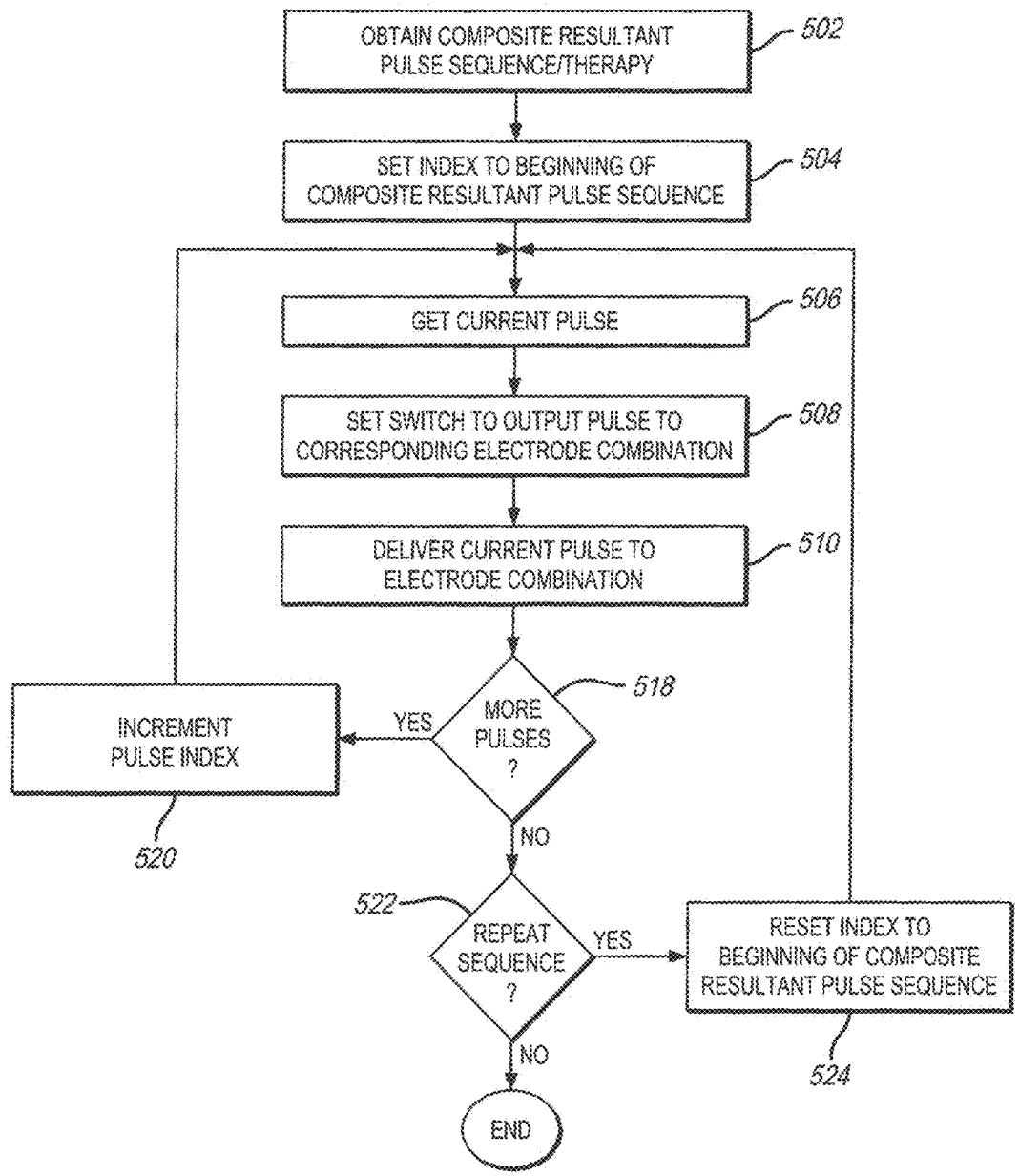
FIG. 5 illustrates the operations implemented by an IMD while delivering a composite resultant pulse sequence in accordance with embodiments herein.

FIG. 5 illustrates the operations implemented by an IMD while delivering a composite resultant pulse sequence. At 502, a controller 151 (FIG. 1C) of the IMD accesses memory within the IMD to obtain the composite resultant pulse sequence (therapy) which comprises at least first and second component sequences of pulse trains. As explained herein, one or more of the pulses from at least one of the resultant pulse trains have been temporally shifted from the target pulse frequency. By way of example, the composite resultant pulse sequence is loaded into a circular buffer utilized to drive the pulse generating circuit. Optionally, the composite resultant pulse sequence may be utilized in alternative hardware configurations to direct the pulse generating circuit to generate CRP sequences.

At 504, the controller 151 of the IMD sets an index into the circular buffer to the beginning of the composite resultant pulse sequence. As explained hereafter, the index is stepped through the circular buffer in connection with managing the pulse generating circuit to produce the composite resultant pulse sequence. The composite resultant pulse sequence represents the combination of pulses having a defined sequence length. The pulse generating circuit repeatedly reproducing the pulse sequence for the total sequence length.

At 506, the controller 151 of the IMD obtains a current pulse. At 508, the processor determines which electrode combination corresponds to the current pulse and sets the switching circuit to be connected to the corresponding electrode combination. At 510, the current pulse is delivered to the corresponding electrode combination. At 518, the controller 151 of the IMD determines whether additional pulses exist in the composite resultant pulse sequence. When additional pulses exist, flow advances to 520. At 520, the controller 151 increments a pulse index into the CRP sequence. Thereafter, flow returns to 506 where the next pulse is obtained. Returning to 518, when no more pulses exist in the CRP sequence, flow moves to 522. At 522, the controller 151 determines whether to repeat the CRP sequence. When the decision at 522 is no, the process ends. Alternatively, when the CRP sequences to be repeated, flow moves to 524. At 524, an index into the composite resultant pulse sequence is reset to the beginning of the composite resultant pulse sequence. Thereafter, flow returns to 506 and the process is repeated.

FIG. 6A illustrates a portion of a composite resultant pulse sequence 602 that may be produced by a pulse generating circuit. The CRP sequence 602 includes individual pulses 604-607 and 614-617. To further illustrate the relation between the pulses in FIG. 6A, crosshatching has been added. Pulses having a common type of crosshatching correspond to a single target pulse train, while pulses having different types of crosshatching correspond to different target pulse trains. With reference to FIGS. 4A-4D, the pulses 604 and 614 may correspond to successive pulses 410 in the first target pulse train 402. Pulses 605, 615 may correspond to successive pulses 418 in the third target pulse train 406. Pulses 606, 616 may correspond to successive pulses 414 in the second target pulse train 404, while pulses 607, 617 may correspond to successive pulses 420 in the fourth target pulse train 408. The foregoing correlation of pulses between the CRP sequence 602 and the individual target pulse trains 604-608 merely represents an example. Alternative combinations may occur. The successive ones of the pulses 602-617 are separated by different successive pulse spacing 641-644. The spacing of the pulses is shifted until the successive pulse spacing equals or is greater than a select limit. The lower limit for the pulse spacing 641-644 may correspond to an amount of time desired to afford capacitor discharge of one or more capacitors in the pulse generating circuit.

In the example of FIG. 6A, the pulses from different pulse trains occur in a common order. Optionally, the pulses from different pulse trains may occur in different orders within groups of pulses from different pulse trains. For example, attention is directed to FIG. 6B. FIG. 6B illustrates a portion of a CRP sequence 620 that includes first through fourth resultant pulse trains that have been shifted to avoid temporal overlap. In FIG. 6B, pulses 624 correspond to one target pulse train, while pulses 626, 627 and 628 correspond to second, third and fourth target pulse trains. As illustrated in FIG. 6B, an un-even number of pulses are presented in connection with separate corresponding target pulse trains. In addition, the order and spacing of successive pulses associated with different pulse trains various. For example, the first pulse 626, associated with the second target pulse train, is positioned between pulses 624 and 627 associated with the first and third target pulse trains. However, the second pulse 626 associated with the second pulse train precedes a pulse 628 associated with the fourth pulse train. The fourth pulse 626 associated with the second pulse train follows a pulse 627 associated with the third pulse train. Optionally, the CRP sequence may include other pulse combinations, orders, differences in pulse width, differences in pulse amplitude and the like.

Method for Calculating Length of Composite Resultant Pulse Sequence

Figure 7:
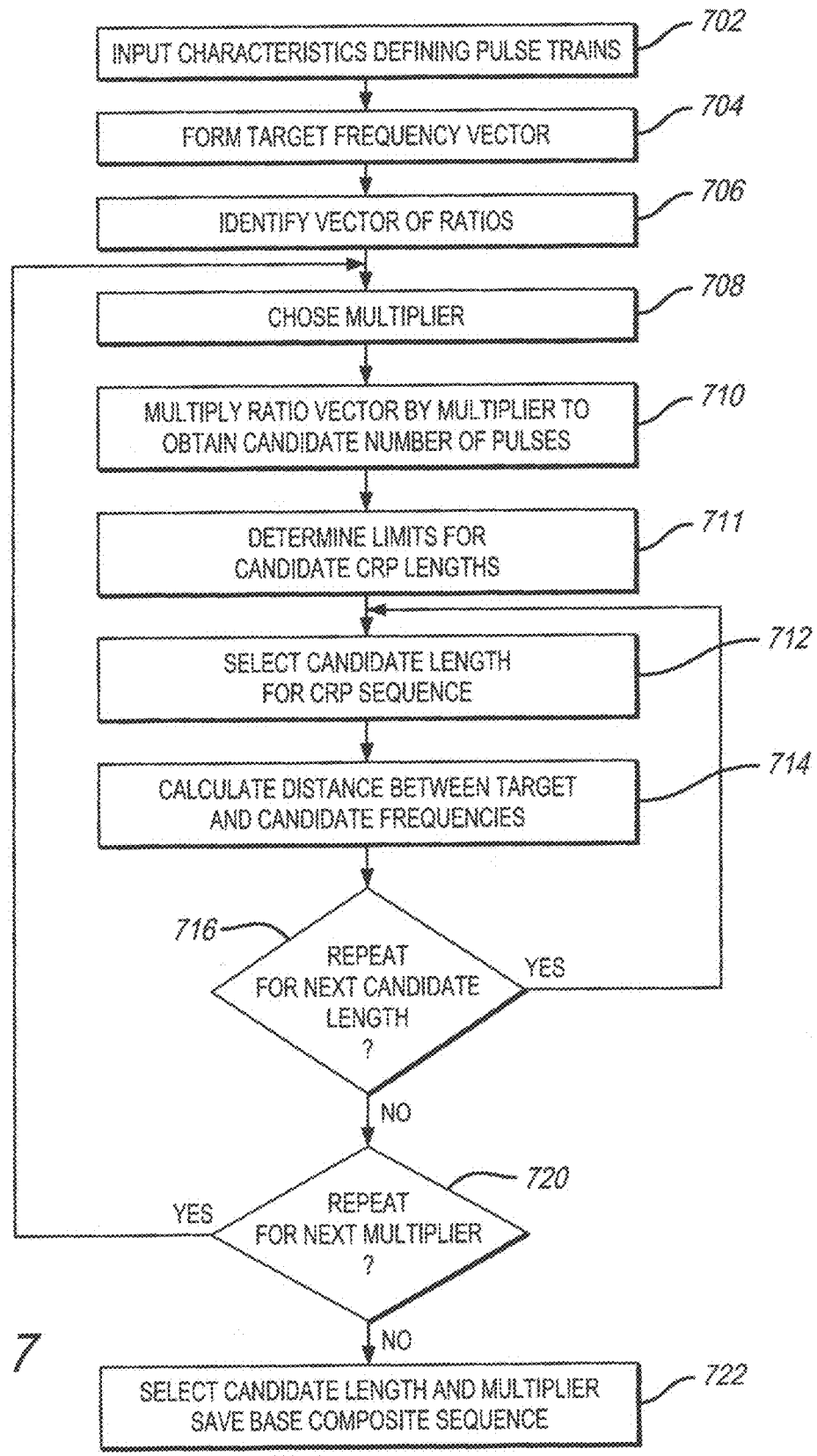
FIG. 7 illustrates an example process for calculating the total length of the composite resultant pulse sequence in accordance with embodiments herein.

FIG. 7 illustrates an example process for calculating the total length of the composite resultant pulse sequence in accordance with embodiments herein. In one or more embodiments, the process of FIG. 7 is carried out by one or more processors of an external device (e.g., 160 in FIG. 1C) separate from the IMD. For example, the external device may represent a physician programmer device, personal computer, laptop computer, workstation, server, table device, smart phone and the like. The process of FIG. 7 also calculates the number of pulses within the CRP sequence associated with each target therapy (corresponding to each target pulse train). While a detailed explanation is provided for at least one embodiment for calculating a composite resultant pulse sequence, it is recognized that other processes may be implemented to calculate the length of the CRP sequence and the number of pulses therein in connection with each target therapy.

At 702, characteristics defining a set of target pulse trains are received. For example, the target pulse trains may be programmed by a physician through an external device, predetermined based on pre-implant planning, programmed during a patient visit after implant of an IMD, automatically determined based on sensor feedback and the like. For purposes of explanation, it is assumed that the common pulse generating circuit is to produce pulse trains $tr_0$, $tr_1 \ldots tr_n$, wherein each train represents a target pulse train that is characterized by a target frequency and target pulse width. The target frequency and target pulse width represent examples of two characteristics that define a target therapy. The pulses from each train are designated to be delivered to a specific location in the body. For purposes of the following discussion, the target frequencies are denoted by $f_0, f_1 \ldots f_n$ and the target pulse widths are denoted by $pw_0, pw_1 \ldots pw_n$.

The external device approximates candidate frequencies that may be used in place of target frequencies for each corresponding target pulse train. To begin the approximation, at 704, one or more processors of the external device form a target frequency vector $f_s$ from the target frequencies. Without loss of generality, it can be assumed that the frequencies have been sorted from lowest to highest (where $f_0$ is the lowest).

$$fs = \begin{pmatrix} f_0 \\ f_1 \\ \ldots \\ f_n \end{pmatrix}$$

In the remaining operations of FIG. 7, the processor(s) of the external device produces a finite sequence of pulses that the IMD processor and pulse generating circuit will execute repeatedly in a loop to deliver all desired therapies. When executed, the CRP sequence includes resultant component sequences that represents a close approximation of the target frequency for each target therapy. In accordance with at least some embodiments, the pulse generating circuit is managed through a digital implementation, and as such the time measurement are in multiples of the clock period (referred to as "TC"). When finalized, the CRP sequence represents a finite sequence that has a length of K clock cycles. Within the CRP sequence, the pulse generator will produce an integer number of pulses $i_0$ for the first target frequency, an integer number of pulses $i_1$ for the second target frequency and so on. It is convenient to write this in a vector form:

$$is = \begin{pmatrix} i_0 \\ i_1 \\ \ldots \\ i_n \end{pmatrix}$$

As the overall time of the finite sequence is K*TC, the actual frequencies produced will be:

$$Fs = \frac{1}{K \cdot TC} \cdot \begin{pmatrix} i_0 \\ i_1 \\ \ldots \\ i_n \end{pmatrix}$$

At 706, the external device identifies a vector of ratios. For example, the vector of ratios may be defined relative to a select one of the frequencies, such as frequency $f_0$, as follows:

$$rs = \begin{pmatrix} r_0 \\ r_1 \\ \ldots \\ r_n \end{pmatrix} = \begin{pmatrix} 1 \\ \frac{f_1}{f_0} \\ \ldots \\ \frac{f_n}{f_0} \end{pmatrix}$$

In the foregoing grouping, $f_0$ represents a zero frequency, $f_1$ represents a first frequency, and $f_n$ represents an $n^{th}$ frequency Next, the process determines the number of pulses (associated with each target pulse train) to include in the CRP sequence. In general, it is desirable for the ratios of the number of candidate pulses in the CRP sequence to be within a select limit of the ratios of frequencies of the target pulses in the original target pulse trains. To identify one or more acceptable numbers of the candidate pulses to include in the CRP sequence for each target pulse train, at 708 a multiplier is chosen. For example, the multiplier may be an integer (e.g. one-100). At 710, the external device multiplies the ratio vector by the multiplier m to obtain candidate numbers of pulses to potentially be included within the CRP sequence in connection with each target therapy:

$$\begin{pmatrix} i_0 \\ i_1 \\ \ldots \\ i_n \end{pmatrix} = m \cdot \begin{pmatrix} r_0 \\ r_1 \\ \ldots \\ r_n \end{pmatrix} = \begin{pmatrix} m \cdot r_0 \\ m \cdot r_1 \\ \ldots \\ m \cdot r_n \end{pmatrix}$$

The products of the multiplier m and each of the ratios in the ratio vector may yield non-integer numbers. Therefore, for a given multiplier m, the process at 710 also rounds the products of the multiplier and ratio vector to form the following vector I(m):

$$I(m) = \begin{pmatrix} \text{round}(m \cdot r_0) \\ \text{round}(m \cdot r_1) \\ \ldots \\ \text{round}(m \cdot r_n) \end{pmatrix}$$

The vector I(m) defines a set of candidate pulse trains. For example, when the product of $m \cdot r_1$, when rounded to a whole number, may equal 5. Thus, the CRP sequence would include 5 pulses, associated with target pulse train $TPT_1$, distributed over the length of the CRP sequence and intended to be delivered as a therapy associated with a target pulse train 1 ($TRT_1$). If the vector I(m) includes a value 8 for $TPT_3$, then the CRP sequence would include 8 pulses distributed over the CRP sequence and intended to be delivered as a therapy associated with a target pulse train 3 ($TRT_3$). Each time the CRP sequence is repeated, the corresponding pulses are repeated.

It is recognized that, the vector I(m) will no longer produce the exact ratios of target frequencies, associated with the target pulse trains, due to the integer rounding. However, for some multiplier(s) m, the ratios may be very close to the target frequencies. The CRP sequence will produce pulses associated with each target therapy at a rate that may be characterized as a "candidate" frequency (e.g., calculated based on the number of pulses delivered for a target therapy and the length of the CRP sequence). The overall duration of the CRP sequence is the number of clock cycles times the duration of one clock cycle, or K*TC. Dividing each component of the vector I(m) by this overall duration gives the candidate frequency for that train. Accordingly, the candidate frequencies can be represented in a vector as follows:

$$fx = \frac{1}{K \cdot TC} \cdot \begin{pmatrix} \text{round}(m \cdot r_0) \\ \text{round}(m \cdot r_1) \\ \ldots \\ \text{round}(m \cdot r_n) \end{pmatrix}$$

The frequency ratios $r_0$ to $r_n$ and TC are known. The multiplier m and the total number of clock cycles K in the CRP sequence are unknown at this stage in the process. The external device implements a calculation to find a pair (m, K) that affords a desired result, such as a pair (m, K) that affords a select (e.g., best) approximation of the required frequencies. The select approximation pair (m, K) may be based on various criteria.

At 711, the patient device determines limits for the candidate CRP lengths that would be viable with the current multiplier. Before selecting the first candidate length, unsuitable the lengths for the CRP sequence are ruled out. The value $K_n$ will produce an exact candidate frequency for output n. Embodiments herein utilize one value for K to define a total length for the CRP sequence, which will serve as a compromise for all frequencies. In connection with calculating the candidate length for the CRP sequence, upper and lower limits our first determined. The following integer values are calculated for the upper and lower limits:

$K_{min} = \text{floor}(\min(K_n))$ $K_{max} = \text{ceil}(\max(K_n))$

The values $K_{min}$ and $K_{max}$ represent a lower limit/floor and an upper limit/ceiling for candidate values for K. Values outside of the interval ($K_{min}$, $K_{max}$) would not obtain a desired result (e.g., could not be optimal). Within that interval ($K_{min}$, $K_{min}$), the patient device tests each value of K. Based on the test, the patient device selects a value for K that affords no more than an outer limit (e.g., minimum distance) for a select distance between the candidate and target frequencies.

At 712, a first candidate length is selected within the limits of potential candidates determined at 711. For example, the upper or lower limit of the range determined at 711 may be utilized. Once the process chooses a multiplier m, based on the following vector, the number of pulses can be determined:

$$\begin{pmatrix} i_0 \\ i_1 \\ \ldots \\ i_n \end{pmatrix} = \begin{pmatrix} \text{round}(m \cdot r_0) \\ \text{round}(m \cdot r_1) \\ \ldots \\ \text{round}(m \cdot r_n) \end{pmatrix}$$

For example, when the ratios $r_1$ and $r_n$ are set as 5 and 7, respectively, and m=3, the number of pulses $i_j$=15 and $i_n$=21. The candidate length for the CRP sequence represents a value for the clock cycles K. The candidate length for the CRP sequence would produce a candidate frequency for each therapy component:

$$K_n = \frac{1}{TC} \cdot \frac{i_n}{f_n}$$

At 714, the patient device calculates a measure of "fitness" (e.g. distance) between the target and candidate frequencies. The relation determined at 714 is based on candidate frequencies that are calculated using the current candidate length and current multiplier. For example, it may be desirable for the vector of resultant frequencies fx to be close in one or more criteria to the target frequency vector fs (denoted below as "f" and "$f_j$"). In accordance with one embodiment, the process defines a distance between the candidate and target frequency vectors. For example, the distance between the candidate and target frequency vectors may be defined as the maximum relative deviation of any frequency component in the candidate and target frequency vectors:

$$dist(fx, f) = \max\left(\left|\frac{fx_i - f_i}{f_i}\right|\right)$$

As one example, a benefit of using the above distance is that when both low and high frequencies are present, both of the high and low frequencies are given the same weight. If, for example Euclidian distance was used, higher frequencies would be fitted to high accuracy while low frequencies would be less accurate.

At 716, the patient device determines whether to repeat the distance calculation in connection with another candidate length for the CRP sequence. When additional candidate lengths are to be tested, flow returns to 714 and a next candidate length is tested. For example, the candidate length may be incremented by a predetermined amount. At 716, when it is determined that no additional candidate lengths should be tested in connection with the present multiplier, flow moves to 720. At 720 is determined whether the overall process should be repeated for a different multiplier. When the process is to be repeated for another multiplier, flow returns to 708 and the multiplier is changed. For example, the multiplier may be incremented by a predetermined amount.

When no additional multipliers are to be tested at 720, flow moves to 722. At 722, the patient device compares the distances that were calculated at 714 for various candidate lengths and multipliers. At 722, the patient device selects a length-multiplier combination that achieves a desired result. The desired result is determined in connection with one or more criteria of interest. For example, the candidate length and multiplier combination, that is selected, may represent the combination that yields a least frequency difference (generally referred to as a distance) between the target and candidate frequencies.

The combination of candidate length and multiplier represent characteristics that define a base composite sequence. The base composite sequence has a length corresponding to the number clock cycles designated by the candidate length. The base composite sequence includes a number pulses associated with each target therapy that is determined by the multiplier and the frequency ratios described above. Optionally, the CRP sequence may be defined by additional characteristics (e.g., pulse width, pulse amplitude, electrode combination). Additionally or alternatively, one or more target therapies may correspond to a tonic type pulse train, while one or more other target therapies may correspond to burst type pulse trains. Accordingly, one or more characteristics that define the base composite sequence may indicate tonic vs. burst therapy. When burst therapy is used, the characteristics may further describe the burst characteristics (e.g., burst length, burst frequency). Thereafter, the process of FIG. 7 ends and a base composite sequence is saved (e.g., see FIG. 10A).

As an example, it is assumed that the system utilizes a clock operating at 50 kHz and that target pulse trains (also corresponding to the target therapies) have the following frequencies: 32 Hz, 57 Hz, 121.5 Hz and 147 Hz.

$$TC := \frac{1}{50 \text{ kHz}} = 20 \text{ } \mu s$$

$$fs := \begin{pmatrix} 32 \\ 57 \\ 121.5 \\ 147 \end{pmatrix} \text{Hz}$$

$$dist(fx, f) := \left( \left| \frac{\overrightarrow{fx - f}}{f} \right| \right)$$

As explained above, the patient device forms the vector of frequency ratios:

$$rs := fs \cdot \frac{1}{fs_0} = \begin{pmatrix} 1 \\ 1.781 \\ 3.797 \\ 4.594 \end{pmatrix}$$

Next, we define the function that will give the number of pulses for any multiplier m:

$$i(m) := \overrightarrow{\text{round}(m \cdot rs)}$$

According to the algorithm, the process starts with m=1. The vector of number of pulses to make is:

$$i(1) = \begin{pmatrix} 1 \\ 2 \\ 4 \\ 5 \end{pmatrix}$$

In order to produce the exact frequencies with these numbers of pulses, the total sequence lengths would be different for each sequence:

$$Kv := \frac{\overrightarrow{i(1)}}{fs} \cdot \frac{1}{TC} = \begin{pmatrix} 1562.5 \\ 1754.386 \\ 1646.0905 \\ 1700.6803 \end{pmatrix}$$

Next, the process picks one value for the total length, where the value is between kmin:=floor (min(Kv))=1562 and kmax:=ceil(max(Kv))=1755

Taking the minimum value of 1562 will produce the following frequencies:

$$fx(k) := \frac{1}{k \cdot TC} \cdot i(1)$$

$$fx(1562) = \begin{pmatrix} 32.01 \\ 64.02 \\ 128.041 \\ 160.051 \end{pmatrix} \text{Hz}$$

The distance between the required vector and the produced vector will be:

$$dist\left[ \begin{pmatrix} 32 \\ 57 \\ 121.5 \\ 147 \end{pmatrix} \text{Hz}, \begin{pmatrix} 32.01 \\ 64.02 \\ 128.041 \\ 160.051 \end{pmatrix} \text{Hz} \right] = 10.965\%$$

If the process plots the distance as a function of the total sequence length K, the select length is K=1653, for which the frequency difference distance becomes 0.0579:

According to the algorithm, the same steps are repeated for m=2, 3, 4 and so on. For example, the result for m=5 is $$i(5) = \begin{pmatrix} 5 \\ 9 \\ 19 \\ 23 \end{pmatrix}$$

The preferred value for K is 7853 cycles of the clock and the generated frequencies are $$fx(7852) = \begin{pmatrix} 31.839 \\ 57.31 \\ 120.988 \\ 146.46 \end{pmatrix} Hz$$

The maximum deviation of any of these frequencies from the required is about 0.5%.

$$dist\left[ \begin{pmatrix} 32 \\ 57 \\ 121.5 \\ 147 \end{pmatrix} Hz, \begin{pmatrix} 31.839 \\ 57.31 \\ 120.988 \\ 146.46 \end{pmatrix} Hz \right] = 0.541\%$$

The result of the calculations is that the system will to produce 5 pulses of the first sequence, 9 pulses of the second, 19 of the third and 23 of the fourth, for a total of 56 pulses. The pulses are dispersed evenly over the total length 7853 clock cycles. With that, all frequencies will be within 0.54% of a preferred value. The resulting sequence represents a base CRP sequence.

As explained herein, it is not practical for a single pulse generating circuit to produce the base CRP sequence due to undesirable pulses overlap. Accordingly, the external device applies a pulse interleaving to reconcile pulse overlap. Pulse interleaving is applied through one or more diffusion algorithms. In general, the idea behind the interleaving is inspired by the physical processes of diffusion. In diffusion, particles of several substances gradually mix over time. The diffusion process is governed by certain physical laws. Embodiments herein implement pulse interleaving by following the same idea, where particles are replaced by pulses and the "physical laws" are defined in a way that will ensure certain properties of the "mixture" of the interleaved stimulation. The base CRP sequence represents an initial state (with overlapping pulses). The interleaving process computationally applies pulse diffusion. The result is a pulse mixture with certain properties.

The properties of the "pulse mixture" are determined by the "physical laws" that may be defined in various manners. For example, a repelling force is defined that is applied between pulses from different pulse trains, where the repelling force grows to be very large as pulses come close. The repelling force achieves a first desirable property of the mixture, namely that the pulses do not overlap in a manner that prevents the pulses from being generated sequentially. As another example, an elastic force is defined that is applied between pulses of the same train, where the elastic force grows as adjacent pulses in a common pulse train move further apart. The elastic force achieves another property of the mixture, namely that pulses in a common pulse train attempt to stay as close as possible to an even, equal spacing in order that the pulse train resembles a single (target) frequency.

By changing the relative strength of these "physical laws", the interleaving process can emphasize one property over the other. While certain processes are described herein to implement the interleaving process, it is understood that alternative algorithms may be implement. For example, a class of algorithms called "genetic algorithms" may be utilized to achieve a desired interleaving relation.

Figure 8:
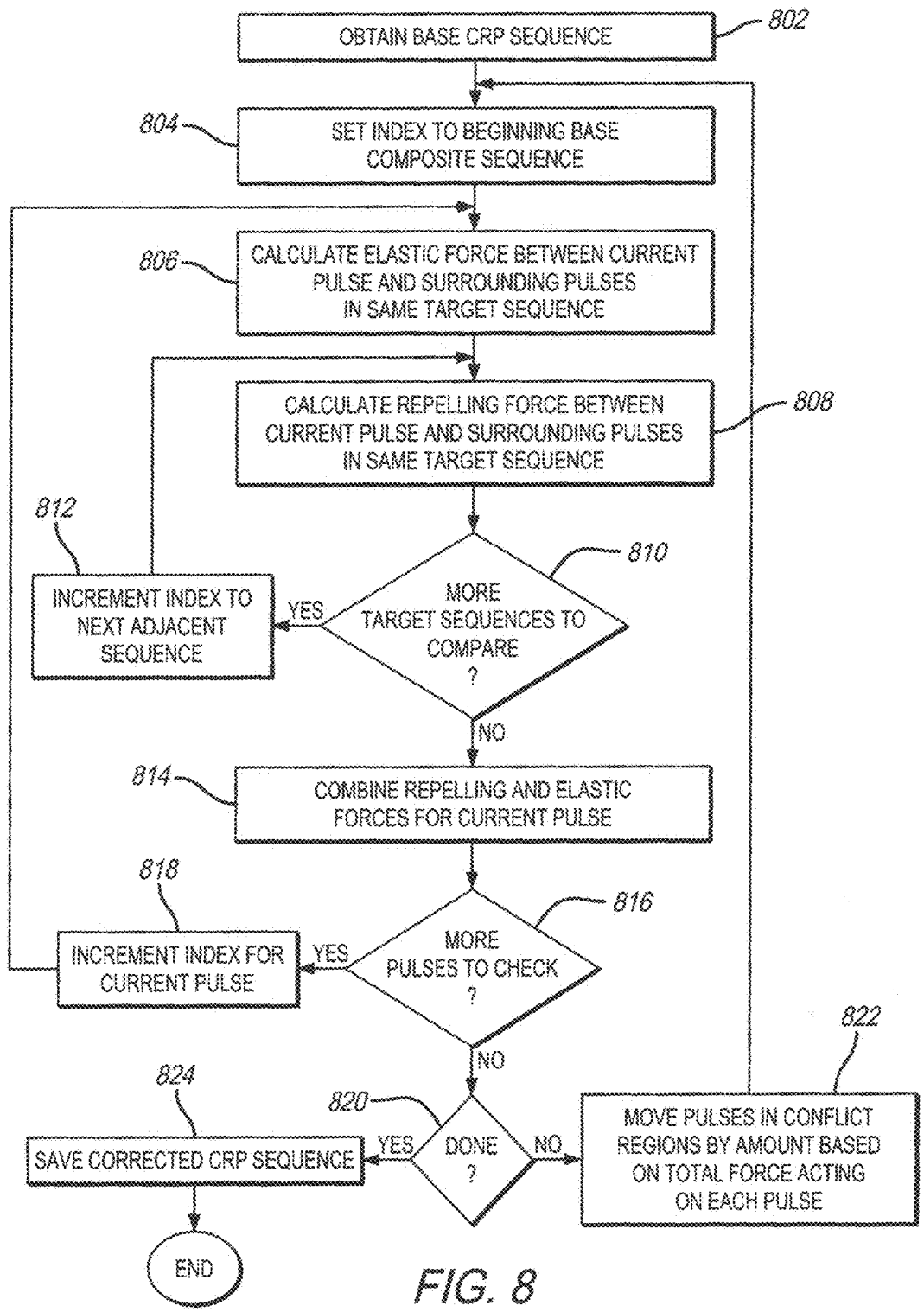
FIG. 8 illustrates a process for reconciling pulse overlap within the base composite sequence in accordance with embodiments herein.

FIG. 8 illustrates an interleaving or diffusion process for reconciling pulse overlap within the base composite sequence in accordance with embodiments herein. To demonstrate how the algorithm reconciles pulse overlap, an example is provided in connection FIGS. 9A-9C and 10A-10B. In the previous example, it was found that the base composite sequence, that would have a length sufficient for the number of pulses desired to approximate four target frequencies, should include 5, 9, 19 and 23 pulses, respectively, for each of the target frequencies/therapies.

Figure 9A:
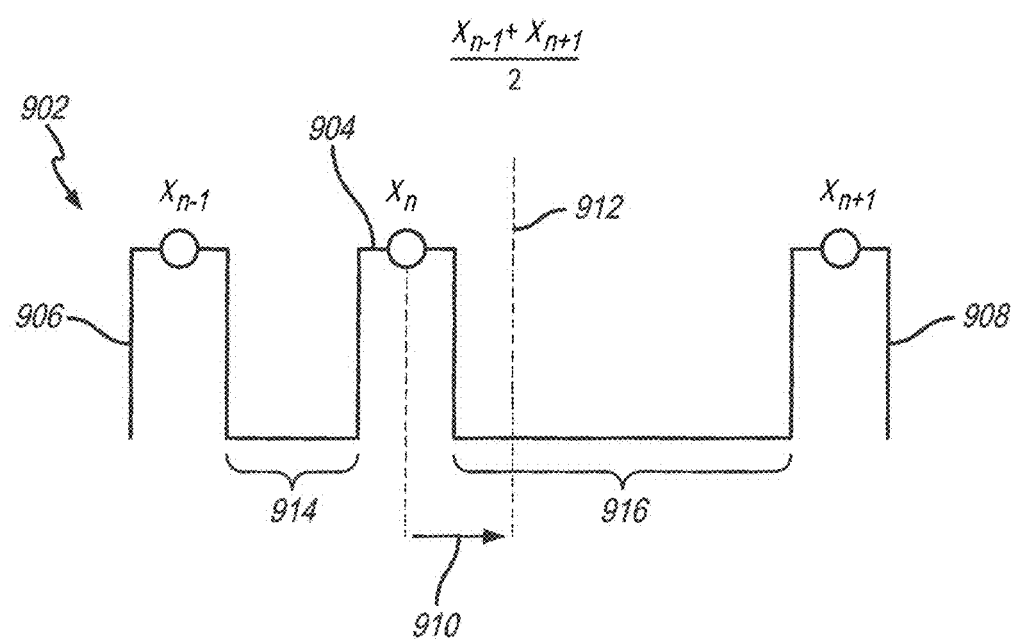
FIG. 9A illustrates a portion of a pulse sequence associated with a single component sequence in accordance with embodiments herein.
Figure 9B:
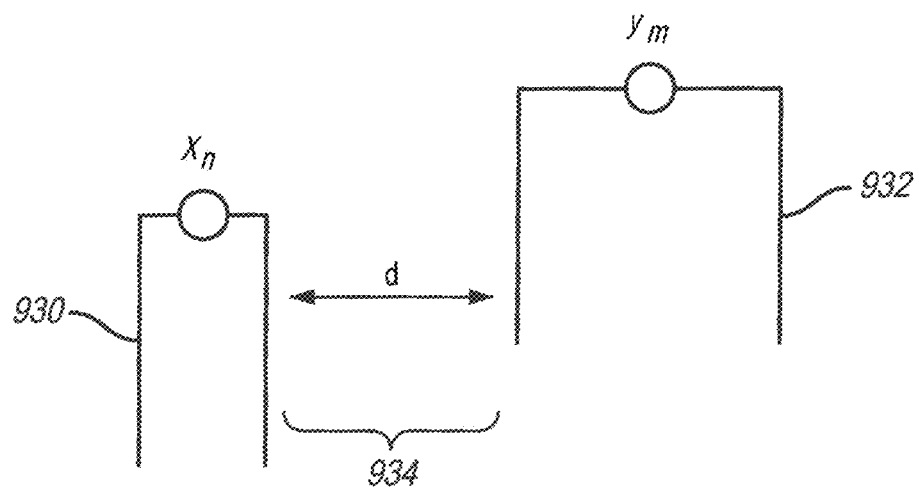
FIG. 9B illustrates a first pulse associated with a first target pulse train and a second pulse associated with a second target pulse train in accordance with embodiments herein.
Figure 9C:
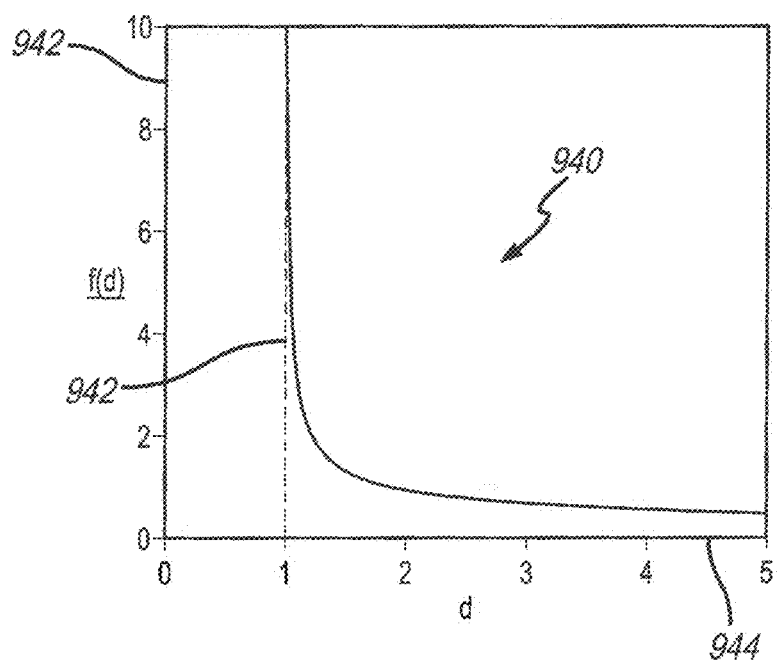
FIG. 9C illustrates a graph plotting a relation between repelling force relative to the distance d between the pulses of FIG. 9B in accordance with embodiments herein.

FIGS. 9A-9C illustrate "elastic force" and "repelling force" principles applied in connection with FIG. 8 to shift pulses.

Figure 10A:
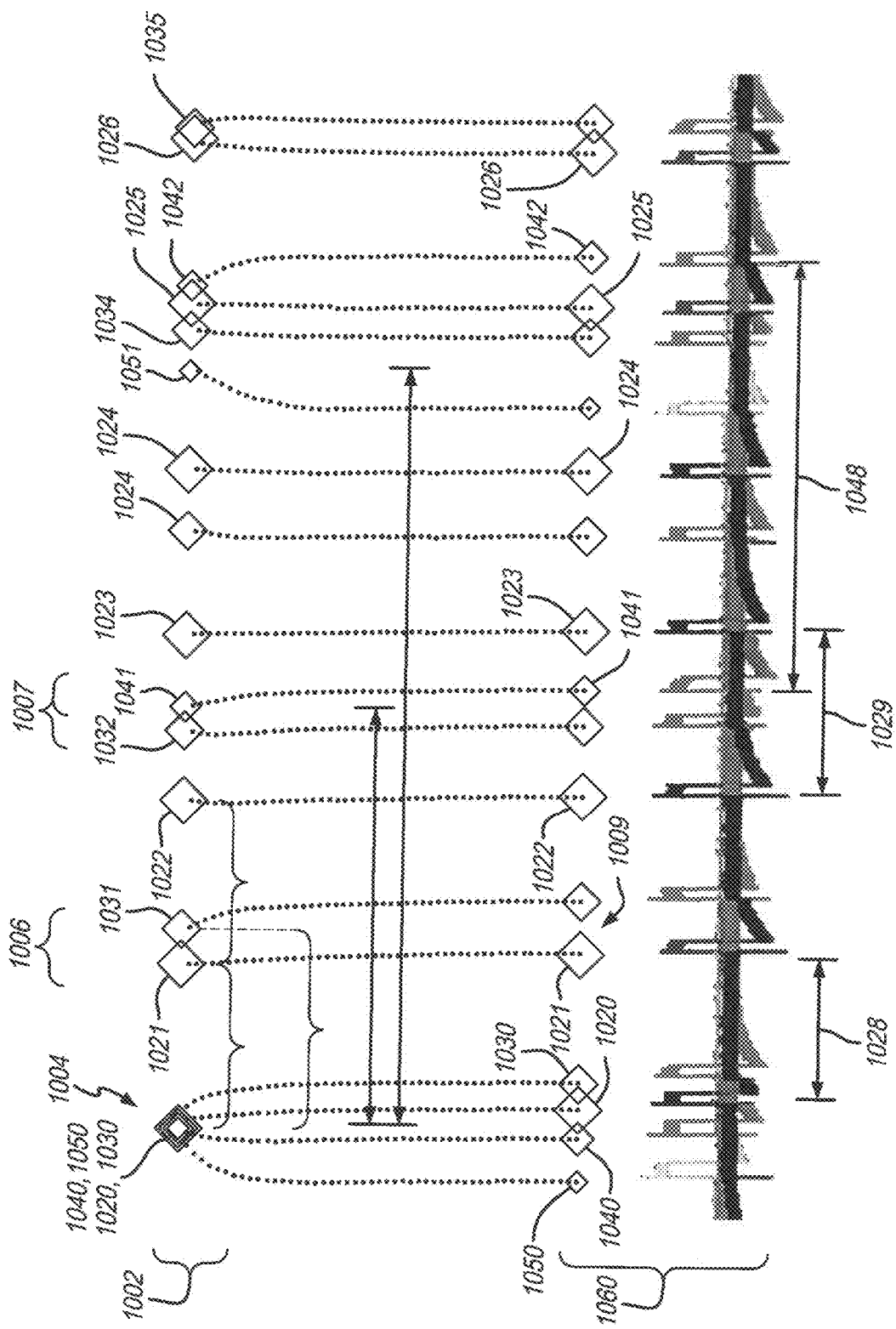
FIG. 10A illustrates an example of a portion of a base composite sequence utilized in accordance with embodiments herein.
Figure 10B:
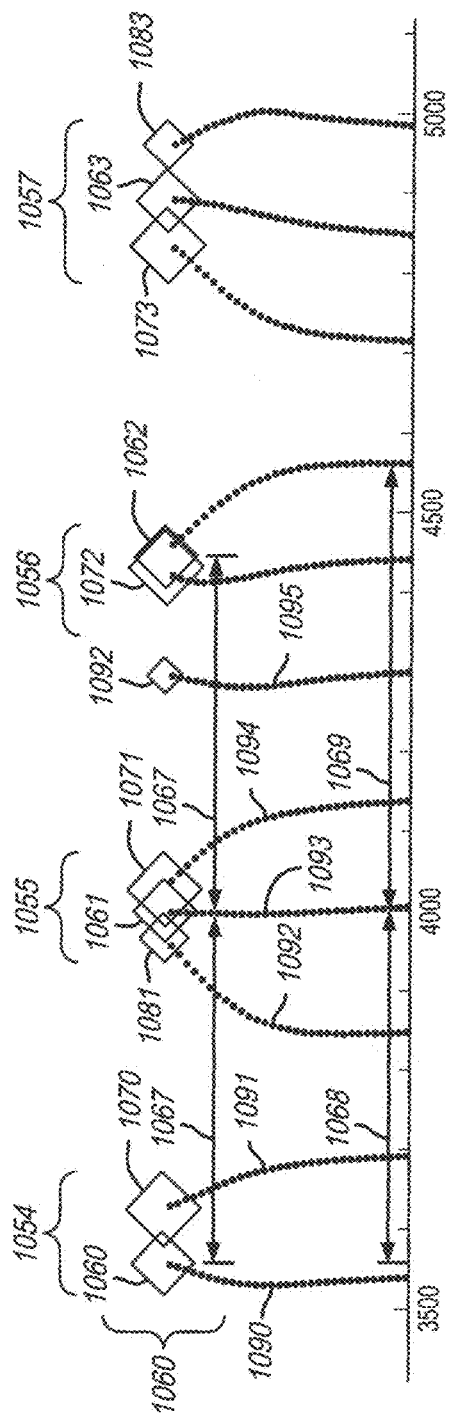
FIG. 10B illustrates an enlarged view of a portion of a base composite sequence that is acted upon in accordance with embodiments herein.

FIGS. 10A-10B illustrate an example of a portion of a base composite sequence 1002 utilized in accordance with embodiments herein. The base composite sequence 1002 comprises pulses from multiple target pulse trains (multiple target therapies). For purposes of illustration, the pulses in the base composite sequence 1002 are illustrated as rectangular blocks of different size. A conflict region 1004 illustrates four pulses that substantially overlap one another. Conflict region 1006 illustrates a pulse 1021 from the first target pulse train $TPT_1$, and a pulse 1031 from a second target pulse train $TPT_2$. In the example of FIG. 10A, the pulses 1020-1026 correspond to the first target pulse train $TPT_1$, while pulses 1030-1035 corresponds to the second target pulse train $TPT_2$. Pulses 1040, 1042 correspond to a third target pulse train and pulses 1050-1051 correspond to a fourth target pulse train. Each of the four target pulse trains include a pulse in conflict region 1004 (but are not separately labeled).

The base composite sequence 1002 illustrates the pulses 1020-1050 when in an initial pulse alignment, such as corresponding to the original target pulse trains and target sequences associated with each target therapy. As explained herein, the base composite sequence 1002 is adjusted based on the elastic forces and repelling forces to temporarily shift one or more of the pulses to avoid overlap in conflict regions until generating a final corrected CRP sequence 1060. The final corrected CRP sequence 1060 is illustrated in two forms, with the upper form indicated as rectangles or diamonds and the lower form corresponding to an example see trace of pulses delivered over time from a capacitor discharge device. The corrected CRP sequence 1060 comprises separate resultant pulse trains that are based on, but temporally shifted from, the original target pulse trains. In the composite pulse sequence 1060, the pulses from the conflict region 1004 have been shifted with respect to one another to avoid conflict and now are visible as distinct pulses 1020, 1030, 1040 and 1050. In the corrected CRP sequence 1060, pulses 1020-1026 form a first component resultant pulse train. The pulses 1030-1035 form a second component resultant pulse train, while pulses 1040-1042 and pulses 1050-1051 form third and fourth component resultant pulse trains.

The pulses 1021 and 1031 in conflict region 1006 are shifted along the time line (forward or backward) relative to starting points in the target pulse train. The pulses 1021 and 1031 are shifted by an amount sufficient to provide a desired successive pulse spacing 1009 there between. Pulses 1022, 1023 and 1024 do not conflict with any other pulse in the base composite sequence 1002, and thus remain in substantially the same position in the base CRP sequence and corrected CRP sequence 1060. The pulses 1032 and 1041 in conflict region 1007 have been shifted slightly to avoid further overlap. The pulse 1051 has been shifted to a substantially intermediate position between pulses 1024 and 1034. The remaining overlapping pulses have also been shifted as illustrated.

When the base composite sequence 1002 is compared to the final corrected CRP sequence 1060, it is apparent that the pulse-to-pulse intervals differ between a target component sequence and the corresponding resultant component sequence. For example, the pulses 1020-1026 of the first component sequence, when in the base composite sequence 1002 are evenly spaced at a pulse-to-pulse interval 1027 across the entire length of the base composite sequence 1002. The pulses 1030-1035 in the second component sequence are also evenly spaced a pulse-to-pulse interval 1037 from one another across the entire length of the base composite sequence 1002. The pulses 1040-1042 of the third component sequence and the pulses 1050-1051 of the fourth component sequence are evenly spaced from one another at the corresponding pulse-to-pulse intervals 1047 and 1057, while in the base composite sequence.

However, the pulses to pulse spacing is adjusted in the final corrected CRP sequence 1060 such that one or more of the component sequences in the final corrected CRP sequence include pulses that are spaced apart from one another by an uneven pulse-to-pulse interval. For example, the first resultant pulse train 1020-1026 includes uneven pulse-to-pulse intervals. For example, the interval 1028 between pulses 1020 and 1021 differs from the interval 1029 between pulses 1022 and 1023. The intervals 1028 and 1029 also differ from the original even interval 1027. As another example, the interval 1048 between pulses 1041 and 1042 differ from one another and differ from the even pulse-to-pulse interval 1047. Each resultant pulse train (e.g., pulse train 1020-1026; pulse train 1030-1035, etc.) includes one or more pulses that are temporally shifted to define corresponding pseudo frequencies that differs from a target pulse frequency of the corresponding target component sequence. For example, pulse train 1020-1026 has one pseudo frequency, while pulse train 1030-1035 has another pseudo frequency. The pseudo frequency is within a select limit or tolerance (e.g., 3-5%, less than 7%) of the target pulse frequency. The pseudo frequency includes an uneven pulse-to-pulse interval between successive pulses in at least one resultant pulse train. Additionally, it may be desirable for the un-even pulse-to-pulse interval to remain within a select limit or tolerance (e.g. within ±15%) with respect to the even pulse-to-pulse interval of the target pulse frequency.

Returning to FIG. 8, next the process for determining the amount of shift is described. In accordance with embodiments herein, the processors manage time shifting pulses to avoid individual pulse trains that have an undue amount of jitter and to avoid pulse trains that differ from the original target pulse train/frequency by an amount greater than a predetermined limit or tolerance. The process of FIG. 8 balances interleaving pulses with maintaining select aspects of each pulse train (e.g., minimize jitter).

At 802, the processor(s) of the external device obtain a base composite sequence from memory (e.g., 1002 in FIG. 10A). At 804, the processor(s) of the external device select a current pulse within base composite sequence. For example, an index may be set to a first position in the base composite sequence.

At 806 and 808, the processor(s) of the external device calculate first and second types of pulse-to-pulse relative factors. Pulses (and burst-type sets of pulses) may be analogized to physical particles, where the location of the particle corresponds to a center of the pulse (or pulse set). When burst type therapies are utilized, the center of an individual burst may be treated as the center of the pulse and the length of the individual burst may be treated as the "pulse width". The pulse-to-pulse relative factors represent conceptual forces, such asn "elastic force" and a "repelling force". Additionally or alternatively, embodiments herein may consider other factors and adjust pulse position based thereon.

At 806, the processor(s) of the external device calculate the "elastic force" type of adjustment between current and surrounding pulses in a corresponding component sequence for a same/common target pulse train/therapy. The elastic force adjustment seeks to shift consecutive pulses, associated with a single target pulse train, to a substantially even pulse-to-pulse spacing. For example, a current pulse of interest may be located at position $x_n$ while preceding and succeeding pulses surrounding the current pulse are at positions $x_{n-1}$ and $x_{n+1}$. Embodiments herein apply the "elastic force" adjustment as a force that is proportional to the relative displacement of the current pulse $x_n$ with respect to the centers of the preceding pulse $x_{n-1}$ and succeeding pulse $x_{n+1}$.

FIG. 9A illustrates a portion of a pulse sequence associated with a single component sequence 902 (also referred to as a target pulse train which has an associated target frequency). The single component structure 902 includes a present/current pulse 904 located between preceding pulse 906 and succeeding pulse 908. In the example of FIG. 9A, the current pulse 904 is initially spaced closer to the preceding pulse 906, as opposed to the succeeding pulse 908. Embodiments herein apply an elastic force calculation that seeks to adjust the position of the current pulse 904 in a direction indicated by elastic force 910. The spacing between the preceding and current pulses 906, 904 represents an intra-therapy pulse spacing 914. The spacing between the current and succeeding pulses 904, 908 also correspond to an intra-therapy pulse spacing 916. The spacing 914, 916 are referred to as "intra-therapy" as successive pulses correspond to a single target pulse train or target therapy. The elastic force 910 seeks to push/shift the center of the current pulse 904 to a target position 912 corresponding to a point halfway between the preceding and succeeding pulses 906, 908. As explained herein, the adjustment suggested by the elastic force 910 represents a proposed shift that through multiple iterations of the process of FIG. 8 is balanced in a compromise with other factors. By way of example, the elastic force 910 may be defined based on the following equation:

$$FE_n = -k \cdot \frac{x_n - \frac{x_{B-1} + x_{n+1}}{2}}{x_{n+1} - x_{n-1}}$$

The constant k is a parameter to t the elastic forest adjustment algorithm referred to as "elastic strength". Optionally, the algorithm may be tuned by varying the constant k: a larger k will produce larger restoring force and will tend to make the sequences more evenly spaced. The elastic forces work to make the pulse sequence evenly spaced. When the sequence is exactly evenly spaced, all elastic forces will be zero. When one or more pulses are displaced from an even spacing, elastic forces occur that seek to restore equal spacing.

In the foregoing example, the elastic force calculation is based on an embodiment in which the spacing between pulses in a pulse train is even. Additionally or alternatively, all or a portion of the pulse train may include pulses, for which the target spacing is a predetermined uneven spacing. When a target pulse train has a predetermined uneven spacing, the elastic force calculation compensates for the uneven spacing and seeks to shift/push the consecutive pulses to positions matching the predetermined uneven spacing of the target pulse train.

At 808, the processor(s) of the external device calculate the second kind of force/adjustment, namely the "repelling force," between the pulses of different pulse trains (different component sequences). The repelling force is calculated based on the distance between i) the current pulse in the current component sequence and ii) one or more surrounding pulses in another/adjacent component sequence. To explain the calculation for the repelling force, relative to one current pulse in a current component sequence and one surrounding pulse in an adjacent component sequence, reference is made to FIG. 9B. FIG. 9B illustrates a first pulse 930 associated with a first target pulse train and a second pulse 932 associated with a second target pulse train. The first pulse 930 corresponds to the current pulse in the current component sequence. The second pulse 932 corresponds to a surrounding pulse in an adjacent/other component sequence. For example, with reference to FIG. 4B, the first and second pulses 930, 932 may correspond to pulses 420 and 418, respectively, in the conflict region 428. The distance d between the pulses 930, 932 is calculated by the one or more processors based on the following equation:

$$d = |y_m - x_n| - \frac{pwx + pwy}{2}$$

In the above equation, the center of the first and second pulses 930, 932 correspond to locations $x_n$ and $y_m$, and the pulse widths of the first and second pulses 930, 932 are defined by the variables $pw_x$ and $pw_y$. The distance d is also referred to as the inter-therapy pulse spacing or the successive pulse spacing 934. The spacing 934 represents an "inter-therapy" spacing as the pulses occur within different target pulse trains or target therapies. In the above equation, the distance d is defined to correspond to the distance between the pulse centers $x_n$ and $y_m$ minus half the pulse width $pw_x$ and $pw_y$ of each pulse. The one or more processors then use the distance d to determine an associated repelling force.

FIG. 9C illustrates a graph 940 plotting a relation between repelling force (as denoted along the vertical axis 942) relative to the distance d (plotted along the horizontal axis 944) between the pulses of FIG. 9B. The graph 940 includes a nonlinear curve defining the repelling force, where the repelling force substantially increases when approaching a predetermined lower limit 943 and the repelling force substantially decreases to a lower limit approaching zero as the distance between successive pulses increases. By way of example, the graph 940 may be defined in accordance with the following equation:

$$f(d) := \begin{vmatrix} \max \leftarrow 10 \\ \mathrm{mind} \leftarrow 1 \\ \mathrm{return\ max\ if\ } d < \mathrm{mind} \\ \frac{1}{(d - \mathrm{mind})^{0.5}} \end{vmatrix}$$

In accordance with the embodiment of FIG. 8, once the distance these determined, the graph 940 is referenced to determine a corresponding repelling force. The repelling force within the graph 940 is defined in such a way that the repelling force approaches a predetermined limit (e.g. becomes infinite) for a value of d equal or less than zero. The predetermined limit is defined such that the pulses never overlap, because as the pulses come close to one another, the repelling force grows infinitely and becomes larger than any elastic forces.

In addition, when the pulses are sufficiently separated, the graph 940 defines the repelling force to decay until becoming negligible. At sufficient separation, the repelling force becomes negligible and the elastic forces dominate and disperse the pulses of same sequences as evenly as possible.

The definition of the graph 940 for the repelling force is quite flexible. Various types of graphs 940 may be defined in which the repelling force generally becomes high as the pulses come close and decays fairly fast as the pulses move apart.

Returning to FIG. 8, the operation at 808 is performed in connection with any surrounding pulses (in adjacent component sequences) that are within a predetermined distance of the current pulse. For example, the operation at 808 may be performed in connection with a single adjacent pulse or multiple adjacent pulses in an adjacent component sequence. The elastic force determined at 806 and the repelling force(s) determined at 808 are combined to form a total force associated with the current pulse in the current component sequence.

At 810, the process determines whether additional component sequences exist that have not yet been compared to the current pulse in the current component sequence. If so, flow moves to 812 where the process increments an index to the next adjacent component sequence. Flow then returns to 808 such that repelling forces are calculated between the current pulse and any surrounding pulses in the next adjacent sequence. Once the pulses in each adjacent sequence are compared to the current pulse in the current sequence, flow moves from 810 to 814.

For example, with reference to FIG. 10A, it may be assumed that a current pulse represents pulse 1041 in a current pulse sequence corresponding to pulses 1040-1042. At 806, the elastic forces are calculated between the current pulse 1041 and the surrounding pulses 1040 and 1042 in the same component sequence (corresponding to a single target pulse train). During one iteration through 808-812, repelling forces are determined between the current pulse 1041 and surrounding pulses 1022, 1023 in an adjacent component sequence (corresponding to pulse train 1020-1026). Not all of the pulses 1020-1026 may be compared to pulse 1041 in connection with determining repelling forces as some of the pulses 1020-1026 may be too far from the current pulse 1041 to impose any repelling force thereon (based upon the graph in FIG. 9C). Once the repelling forces are calculated for the current pulse 1041 with respect to any surrounding pulses of interest from the pulse train associated with pulses 1020-1026, flow steps through operations 810 and 812. At 812, a new adjacent component sequence is identified, such as the pulses 1030-1035 in another component sequence. During the second iteration through 808, repelling forces are calculated between the current pulse 1041 and the surrounding pulses (e.g. 1031-1033) in the next adjacent component sequence. The operations at 808-812 are repeated again in connection with determining any repelling forces between the pulse 1041 and the pulses 1050, 1051 in the final component sequence. Once the current pulse 1041 has been compared relative to any surrounding pulses in the adjacent component sequences, flow advances to 814.

At 814, all of the repelling and elastic forces associated with the current pulse 1041 are combined to form a total force vector (having a magnitude and direction).

At 816, the process determines whether additional pulses remained to be checked. In the foregoing example, after processing the pulse 1041, the process may step to the next pulse in the base composite sequence (e.g. pulse 1023). Consequently, flow moves from 816 to 818. At 818, the process increments the index to the next pulse 1023 and flow returns to 806. The operations at 806 through 814 are repeated in connection with a new current pulse 1023 in order to calculate a total force impose thereon due to elastic forces from surrounding pulses (e.g. 1022, 1024) in the same component sequence (e.g., 1020-1026) and repelling forces from surrounding pulses in adjacent component sequences (e.g. pulses 1032, 1041, 1033, 1051).

In the present example, the process steps through each pulse in sequential order in the CRP sequence. Optionally, the process may step through the pulses associated with a single component sequence and then repeat the process in connection with the pulses in the next component sequence, etc. Ultimately, when the decision at 816 determines that no more pulses exist, flow moves to 820.

At 820, the processors of the external device determine whether the overall analysis operation is done. For example, at 820, it may be determined whether all of the pulses in the base composite sequence are spaced at least a minimum distance apart from one another. When the pulses are not spaced at least a minimum predetermined delay from one another, flow moves to 822. At 822, the processors of the external device shifts the pulses of the base composite sequence such that the pulses are shifted within conflict regions by an amount based on the total force determined to be acting upon each corresponding pulse. The amount and direction of shift is based on the magnitude and direction of the total force. The magnitude of the shift may be based on integer multiples of clock cycles, such as 1-10 clock cycles. Optionally, the magnitude of the shift may be based on a reference time line, such as 1 to X millisecond. The direction in which a pulse is shifted forward in time or backward in time is based on the direction of the total force that is determined to act upon the corresponding pulse. For example, the total shift may correspond to a shift forward in time by 1 clock cycle. As another example the total shift may correspond to a shift backward in time by 2 clock cycles.

With reference to FIG. 10A, it may be determined that a substantial repelling force exist at the conflict region 1004. Accordingly, each of the pulses may be shifted by a substantial proportional amount. As another example, in conflict region 1006, it may be determined that the total force acting upon pulse 1031 is relatively minimal, while the total force acting upon pulse 1021 is very small (relative to other total forces). Accordingly, the pulse 1021 may be shifted very slightly or not all, while the pulse 1031 is shifted slightly more, relative to the amount of shift in pulse 1021.

Once the pulses have been shifted at 822, flow returns to 804 where the updated CRP sequence is again analyzed to identify new elastic and repelling forces associated with each pulse. When the process concludes at 820 that the pulses are sufficiently far apart, flow then advances to 824 where the final corrected CRP sequence is saved to be utilized to drive the IMD. The pulses to pulse spacing is adjusted in the final corrected CRP sequence (e.g., 1060 in FIG. 10A) such that one or more of the component sequences in the final corrected CRP sequence include pulses that are spaced apart from one another by an uneven pulse-to-pulse interval. The process may be repeated until adjacent pulses have at least a minimum successive pulse spacing (e.g., 641-644 in FIG. 6A), but still maintain the uneven pulse-to-pulse interval within a select tolerance of an even pulse-to-pulse interval corresponding to a target pulse frequency of the corresponding target component sequence. For example, it may be desirable to have a successive pulse spacing of at least 0.5 ms. As another example, it may be desirable for the un-even pulse-to-pulse interval to remain within a select tolerance of ±15% with respect to the even pulse-to-pulse interval of the target pulse frequency.

FIG. 10B illustrates an enlarged view of a portion of a base composite sequence that is acted upon in accordance with embodiments herein. The base composite sequence includes conflict regions 1054-1057. The conflict region 1054 includes pulses 1060 and 1070 associated with two different component sequences/therapies. The conflict region 1055 includes pulses 1061, 1071 and 1081 associated with three different component sequences/therapies. The conflict regions 1056 and 1057 include pulses 1062-1092 associated with corresponding component sequences/therapies. The pulses 1060-1063 correspond to a first component sequence. The pulses 1070-1073 correspond to a second component sequence. The pulses 1080-1083 and 1090-1093 correspond to third and fourth component sequences.

During one iteration through FIG. 8, the processors of the external device may determine that the 1060 and 1070 experience slight total forces in opposite directions. Consequently, at 822, the positions of pulses 1060 and 1070 are shifted slightly in opposite directions (pulse 1070 being shifted forward in time one or more clock cycles, while pulse 1060 is shifted backwards in time one or more clock cycles.

As another example, during one iteration through FIG. 8, the processors of the external device may determine that, within conflict region 1055, pulses 1061, 1071 and 1081 experience substantial total forces thereon. Consequently, pulse 1081 may be shifted backwards in time more than one clock cycle, while pulse 1071 is shifted forwards in time at least one clock cycle. In the example of FIG. 10B, pulse 1061 is not shifted, but instead remains at its original clock cycle. As one example, the pulse 1061 may be maintained at its original clock cycle due in part to elastic forces imposed thereon by the surrounding pulses 1060 and 1062 in the same component sequence. In contrast, pulse 1081 does not have surrounding pulses in the same component sequence located as closely to pulse 1081 as the relation between pulses 1060-1062. Consequently, a lesser elastic force may be imposed on pulse 1081, resulting in a greater total force dominated by the repelling forces imposed by the conflict between pulses 1061-1081.

The component sequences, within the base composite sequence 1052, still include even pulse-to-pulse intervals. For example, the pulses 1060-1063 of the first component sequence are evenly spaced at a pulse-to-pulse interval 1067 across the entire length of the base composite sequence. However, after correcting for overlap, the pulse-to-pulse spacing of the first component sequence is adjusted such that the pulses 1060-1063 are spaced apart from one another by uneven pulse-to-pulse interval 1068, 1069. The interval 1067 between pulses 1060 and 1061, differs from the interval 1068 (between pulses 1061, 1062) and the interval 1069 (between pulses 1062 and 1063).

Optionally, each iteration through the process of FIG. 8, may involve a small or large change in the position of various pulses. By way of example, with respect to FIG. 10 B, dotted lines (referred to as trajectories 1090-1095) are illustrated with respect to various pulses. The trajectories 1090-1095 include multiple dots. As one example, a single dot along an individual trajectory 1090-1095 may correspond to one adjustment in the position of a pulse. Alternatively, multiple dots along a trajectory 1090 may correspond to the amount of shift imposed during one force test (e.g. one iteration through FIG. 8).

Optionally, the pulses associated with different component sequences may be shifted at different rates. For example, in the example of FIG. 10 B, the pulses 1081-1083 and 1070-1073 correspond to separate first and second component sequences. The pulses 1081-1083 may be shifted at a faster rate (e.g. multiple clock cycles per force test/shift) as compared to the rate at which the pulses 1070-1073 are shifted (e.g. one clock cycle per shift/iteration through FIG. 8). As one example, the amount of shift introduced during each force test may be based on the number of pulses in the corresponding component sequence in the overall CRP sequence, based on various criteria. Examples of the criteria include the number of pulses within a conflict region, based on the number of conflicts experienced by the pulses of an individual component sequence, etc.

As explained above, the process for interleaving pulses in a non-overlapping manner includes a number of successive operations for calculating the total forces acting on each pulse and moving the pulse a slight amount forward or backward in time based on the total force. Ultimately, the process reaches a predetermined amount of balance, in the interleaved state, to form a composite resultant pulse sequence to be used when delivering the various therapies. As one example, the force test of FIG. 8 may be repeated until each pulse is separated from all other pulses by a predetermined limit for the successive pulse spacing (FIG. 6A) and within the tolerance for the pulse-o-pulse interval. For example, the process may repeat until the spacing is at least 50 μsec, and the tolerance is between 3-5%.

As another example, the force test may be repeated a predetermined limited number of times (e.g. 10 times, 100 times, etc.). After the limited number of force tests, the final combination of pulse positions is utilized. In the event that conflict regions remain, as one option, a pulse may be deleted entirely. For example, when the final/corrected CRP sequence includes first and second adjacent pulses (from different component sequences/therapies) that still unduly overlap one of the first and second adjacent pulses may be deleted from the correct CPR sequence. Optionally, when the final/corrected CRP sequence includes first and second adjacent pulses (from different component sequences/therapies) that still unduly overlap, the first and second adjacent pulses may be utilized during separate successive deliveries of the corrected CRP sequence. For example, during one delivery of the CRP sequence, the first adjacent pulse may be delivered in accordance with a first component sequence/therapy (while the second adjacent pulse is omitted entirely). During a next delivery of the CRP sequence, the second adjacent pulse may be delivered in accordance with a second component sequence/therapy (while the first adjacent pulse is omitted entirely).

Optionally, the foregoing process may be modified or tuned based upon various criteria. For example, the process may be modified to accept a higher amount of jitter in exchange for more even pulse spacing. As one example, a higher amount of jitter may be accepted by decreasing the elastic constant. By decreasing the elastic constant, the elastic forces are weakened as compared to the repelling forces. As the elastic threes are the forces trying to produce an even, low-jitter sequence, jitter will increase. At the same time, the repelling forces will bring about a pulse distribution that is relatively steady state where the capacitors are afforded a maximum time to discharge after every pulse.

Optionally, in accordance with another embodiment, more than one pulse generating circuit may be utilized. When the hardware of the IMD includes two pulse generating circuits, the pulse generating circuits have separate discharge paths to corresponding different electrode combinations. When separate discharge paths are provided, a pulse on one path does not interrupt the discharge on the other path. In the present example, the repelling force can be modified.

Figure 11:
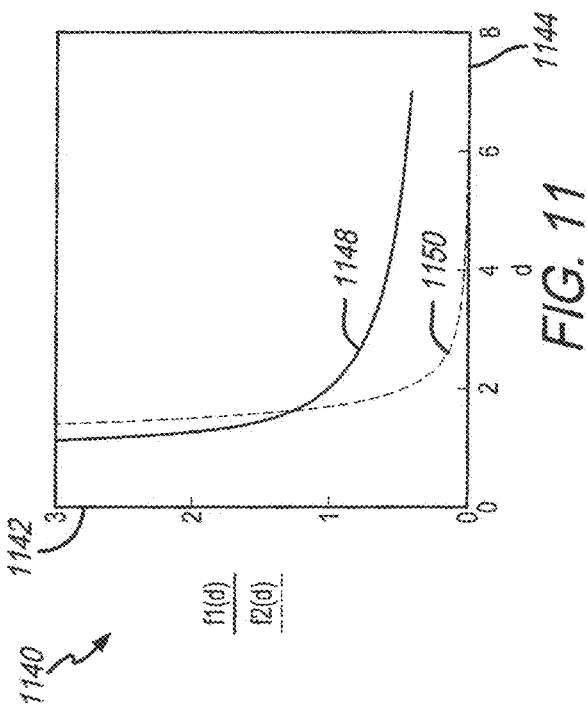
FIG. 11 illustrates a graph plotting two relations between repelling forces relative to the distance between corresponding pulses in accordance with embodiments herein.

FIG. 11 illustrates a graph 1140 plotting two relations between repelling forces (as denoted along the vertical axis 1142) relative to the distance d (plotted along the horizontal axis 1144) between corresponding pulses. The graph 1140 includes two nonlinear curves defining the corresponding repelling forces, where the repelling force substantially increases when approaching a predetermined lower limit and the repelling force substantially decreases to a lower limit approaching zero as the distance between successive pulses increases. The solid line 1148 is the repelling force between two pulses that are produced by a common pulse generating circuit. Because the force decays slower, the pulses would repel each other at greater distances from one another. The force between a pulse produced by one generator and a pulse produced by another generator is defined by the dotted line 1150. As the force decays very fast, the pulses produced by different generators repel each other just enough not to overlap. In the foregoing manner, the process automatically takes advantage of the two generators and fully utilizes the available discharge time.

The characteristics discussed herein represent non-limiting examples of therapy parameters that may be varied to define different nested therapies. For example, a non-limiting list of potential therapy parameters include pulse amplitude, pulse frequency, pulse-to-pulse period, the number of pulses in each burst, burst length, interburst delay, the number of pulse bursts in each interleaved stimulation waveform and the like. The pulse bursts may include pulses having a frequency corresponding to intrinsic neural oscillations exhibited by normal/physiologic brain tissue of interest. The pulse bursts are separated from one another with a burst to burst period that corresponds to a frequency of the low-frequency intrinsic neural oscillations exhibited by normal/physiologic brain tissue of interest.

While the examples of FIGS. 7-11 have been described with respect to operations by an external device, it is understood that all or a portion the operations of FIGS. 7-11 may be divided between two or more external devices. For example, one external device may calculate the base CRP sequence, while another external device calculates applies the interleaving process. As another option, the IMD may perform all or a portion of the operations of FIGS. 7-11. For example, the IMD may receive a base CRP sequence calculated by an external device, with the IMD applying an interleaving process. As another example, a reference set of base CRP sequences may be saved on a host server (e.g., hospital or device manufacturer server). A local or client external device (or an IMD) may access the reference set of CRP sequences and choose one of the reference set of base CRP sequences based on inputs from a physician related to a particular patient's suggested or programmed treatment. The client external device may then apply the interleaving process to determine the CRP sequence to be used. Optionally, the client external device may provide inputs to the host server, from which the host server then performs the interleaving process to return the CRP sequence to the local external device.

Deep Brain Stimulation

In certain embodiments, for example, patients may have an electrical stimulation lead or electrode implanted into the brain. The anatomical targets or predetermined site may be stimulated directly or affected through stimulation in another region of the brain.

In embodiments herein, the predetermined site or implant sites include, but are not limited to thalamus/sub-thalamus, basal ganglia, hippocampus, amygdala, hypothalamus, mammilary bodies, substantia nigra or cortex or white matter tracts afferent to or efferent from the abovementioned brain tissue, inclusive of the corpus callosum. Still further, the predetermined site may comprise the auditory cortex and/or somatosensory cortex in which the stimulation devices are implanted cortically.

Once electrical stimulation lead 14, 110 has been positioned in the brain, lead 14, 110 is uncoupled from any stereotactic equipment present, and the cannula and stereotactic equipment are removed. Where stereotactic equipment is used, the cannula may be removed before, during, or after removal of the stereotactic equipment. Connecting portion 16 of electrical stimulation lead 14, 110 is laid substantially flat along the skull. Where appropriate, any burr hole cover seated in the burr hole may be used to secure electrical stimulation lead 14, 110 in position and possibly to help prevent leakage from the burr hole and entry of contaminants into the burr hole.

Once electrical stimulation lead 14, 110 has been inserted and secured, connecting portion of lead 14, 110 extends from the lead insertion site to the implant site at which IMD 12, 150 is implanted. The implant site is typically a subcutaneous pocket formed to receive and house IMD 12, 150. The implant site is usually positioned a distance away from the insertion site, such as near the chest, below the clavicle or alternatively near the buttocks or another place in the torso area. Once all appropriate components of stimulation system 10, 100 are implanted, these components may be subject to mechanical forces and movement in response to movement of the person's body. A doctor, the patient, or another user of IMD 12, 150 may directly or in directly input signal parameters for controlling the nature of the electrical stimulation provided.

Although example steps are illustrated and described, embodiments herein contemplate two or more steps taking place substantially simultaneously or in a different order. In addition, embodiments herein contemplate using methods with additional steps, fewer steps, or different steps, so long as the steps remain appropriate for implanting an example stimulation system 10, 100 into a person for electrical stimulation of the person's brain.

Brainstem Stimulation

The stimulation system 10, 100, described above, can be implanted into a person's body with stimulation lead 14 located in communication with a predetermined brainstem tissue and/or area. Such systems that can be used are described in WO2004062470, which is incorporated herein by reference in its entirety.

The predetermined brainstem tissue can be selected from medulla oblongata, pons or mesencephalon, more particular the posterior pons or posterior mesencephalon, Lushka's foramen, and ventrolateral part of the medulla oblongata.

In certain embodiments, electrical stimulation lead 14 is located at least partially within or below the aura mater adjacent the brainstem. Alternatively, a stimulation lead 14 can be placed in communication with the predetermined brainstem area by threading the stimulation lead up the spinal cord column, as described above, which is incorporated herein.

As described above, each of the one or more leads 14 incorporated in stimulation system 10 includes one or more electrodes 18 adapted to be positioned near the target brain tissue and used to deliver electrical stimulation energy to the target brain tissue in response to electrical signals received from IMD 12. A percutaneous lead 14 may include one or more circumferential electrodes 18 spaced apart from one another along the length of lead 14. Circumferential electrodes 18 emit electrical stimulation energy generally radially in all directions and may be inserted percutaneously or through a needle. The electrodes 18 of a percutaneous lead 14 may be arranged in configurations other than circumferentially, for example as in a "coated" lead 14. A laminotomy or paddle style lead 14, such as example leads 14e-i, includes one or more directional electrodes 18 spaced apart from one another along one surface of lead 14. Directional electrodes 18 emit electrical stimulation energy in a direction generally perpendicular to the surface of lead 14 on which they are located. Although various types of leads 14 are shown as examples, embodiments herein contemplate stimulation system 10 including any suitable type of lead 14 in any suitable number, including three-dimensional leads and matrix leads as described below. In addition, the leads may be used alone or in combination.

Yet further, a stimulation lead 14 can be implanted in communication with the predetermined brainstem area by a using stereotactic procedures similar to those described above, which are incorporated herein, for implantation via the cerebrum.

Still further, a predetermined brainstem area can be in directly stimulated by implanting a stimulation lead 14 in communication with a cranial nerve (e.g., olfactory nerve, optic, nerve, oculomoter nerve, trochlear nerve, trigeminal nerve, abducent nerve, facial nerve, vestibulocochlear nerve, glossopharyngeal nerve, vagal nerve, accessory nerve, and the hypoglossal nerve) as well as high cervical nerves (cervical nerves have anastomoses with lower cranial nerves) such that stimulation of a cranial nerve in directly stimulates the predetermined brainstem tissue. Such techniques are further described in U.S. Pat. Nos. 6,721,603; 6,622,047; and 5,335,657, and U.S. Provisional Application 60/591,195 entitled "Stimulation System and Method for Treating a Neurological Disorder" each of which are incorporated herein by reference.

Motor Disorders

In Parkinson's disease (PD), the striatum is viewed as the principal input structure of the basal ganglia, while the internal pallidal segment (GPi) and the substantia nigra pars reticulata (SNr) are output structures. Input and output structures are linked via a monosynaptic "direct" pathway and a polysynaptic "indirect" pathway involving the external pallidal segment (GPe) and the subthalamic nucleus (STN). According to current schemes, striatal dopamine (DA)

enhances transmission along the direct pathway (via D1 receptors), and reduces transmission over the indirect pathway (via D2 receptors) (Wichmann and DeLong 2003).

Increased firing rates are noted in PD, both in the globus pallidus (Magnin et al., 2000) and the subthalamic nucleus (Levy et al., 2002) and is reversed in successful STN stimulation in PD (Welter et al., 2004; Boraud et al., 1996). In PD, a (hyper)synchronization is related to tremor (Levy et al., 2002), similarly to what is seen in the animal Parkinson model (Raz et al., 2000; Nini et al, 1995).

Two or more firing modes exist in the subthalamic nucleus: tonic firing (68%), phasic or burst firing (25%) and phasic-tonic (7%) (Magarinos-Ascone et al., 2002).

In the monkey MPTP Parkinson model, burst firing, which occurs at 4 to 8 Hz, increases in the STN and Gpi in comparison to normal firing (from 69% and 78% in STN and GPi to 79% and 89%, respectively) (Bergman et al., 1994), as well as burst duration, without increase in the amount of spikes per burst (Bergman et al., 1994). Abnormally increased tonic and phasic activity in STN leads to abnormal GPi activity and is a major factor in the development of parkinsonian motor signs (Wichmann et al., 1994). The percentage of cells with 4- to 8-Hz periodic activity correlates with tremor and is significantly increased from 2% to 16% in STN and from 0.6% to 25% in GPi with the MPTP treatment (Bergman et al., 1994). These cells are also recorded in humans with PD (Hutchison et al., 1997). Furthermore, synchronization increases, e.g., a decrease in independent activity (Raz et al., 2000; Nini et al., 1995), both in tonically firing cells (Raz et al., 2001) and burst firing cells. Thus, it is envisioned that that the neuromodulation or stimulation system or method of embodiments herein will alter or disrupt or override the regular bursting rhythm associated with PD.

Other movement disorders, for example, chorea, Huntington's chorea, hemiballism and parkinsonian tremor all differ in the amount of regularity in their muscle contractions. (Hashimoto and Yanagisawa 1994). The regularities of interval, amplitude, rise time, and EMG activity differs within order of regularity, such PD, vascular chorea, Huntington chorea and hemiballism being least regular (Hashimoto and Yanagisawa 1994). However, in chorea (Hashimoto et al., 2001), hemiballism (Postuma and Lang 2003) and Huntington's disease (Cubo et al., 2000), the firing rate might be decreased in contrast to PD. Burst discharges are, however, correlated to the choreatic movements (Kanazawa et al., 1990), similarly to what is noted in PD (Bergman, Wichmann et al., 1994). Thus, the neuromodulation system and/or method of embodiments herein is used to alter or disrupt the dysfunctional firing rate of the disease or condition.

Autonomic Disorders

The autonomic nervous system (ANS) is predominantly an efferent system transmitting impulses from the central nervous system (CNS) to peripheral organ systems. Its effects include control of heart rate and force of contraction, constriction and dilatation of blood vessels, contraction and relaxation of smooth muscle in various organs, visual accommodation, pupillary size and secretions from exocrine and endocrine glands. In addition to it being predominantly an efferent system, there are some afferent autonomic fibers (e.g., transmit information from the periphery to the CNS), which are concerned with the mediation of visceral sensation and the regulation of vasomotor and respiratory reflexes, for example the baroreceptors and chemoreceptors in the carotid sinus and aortic arch which are important in the control of heart rate, blood pressure and respiratory activity. These afferent fibers are usually carried to the CNS by major autonomic nerves such as the vagus, splanchnic or pelvic nerves, although afferent pain fibers from blood vessels may be carried by somatic nerves.

The ANS is divided into two separate divisions, the parasympathetic and sympathetic systems. This division is based on anatomical and functional differences. Both of these systems consist of myelinated preganglionic fibres that make synaptic connections with umnyelinated postganglionic fibres, and it is these which then innervate the effector organ. These synapses usually occur in clusters called ganglia. Most organs are innervated by fibers from both divisions of the ANS, and the influence is usually opposing (e.g., the vagus slows the heart, whilst the sympathetic nerves increase its rate and contractility), although it may be parallel (e.g., the salivary glands).

The activity recorded from mammalian sympathetic nerves comes in bursts, which result from large numbers of fibers firing synchronously. Human sympathetic nerve activity behaves similarly. Vasomotor, cardiac and sudomotor nerve fibers all fire in bursts. Bursts in post-ganglionic nerves are driven by synchronously firing preganglionic neurons. Burst amplitude, which reflects the number of fibers firing together, and burst probability are controlled independently (McAllen and Malpas 1997). The sympathetic nerve also fires in a 10 Hz tonic mode (Barman, Kitchens et al., 1997). This 10-Hz rhythm is also involved in cardiovascular regulation, as blood pressure falls significantly when the 10-Hz rhythm is eliminated. Cardiac-related burst activity and 10-Hz rhythms are generated by different pools of brainstem neurons (Barman, Kitchens et al., 1997).

When electrical stimulation is applied to the sympathetic nerve, burst stimulation is more powerful (vasoconstrictor) than tonic mode. The amount of pulses per burst also determines the efficacy of stimulation (Ando, Imaizumi et al., 1993). The same is seen with electrical stimulation of the cervical sympathetic nerve trunk delivered at 50 Hz in bursts of 1 s every 10 s. Burst stimulation evoked a more copious, uniform and reproducible flow of saliva than when delivered at 10 Hz continuously (Anderson, Garrett et al., 1988). Similar superior results with burst stimulation have been obtained studying nasal mucosa reactivity: both types of stimulation reduced nasal blood flow and volume, but the responses were significantly larger with burst stimulation at 0.59 Hz compared to tonic 0.59 Hz stimulation (Lacroix, Stjarne et al., 1988).

In the parasympathetic system, burst firing and tonic firing co-exist. For example, one population of neurons responds with a brief burst of action potentials at the onset of the depolarization, accommodating to the stimulus, and the other population responds with repetitive action potentials persisting throughout the duration of the stimulus, not accommodating to the stimulus (Myers 1998; Bertrand 2004).

The autonomic nervous system plays an important role in the genesis of various cardiac rhythm disorders. In patients with paroxysmal atrial fibrillation, it is important to distinguish vagally mediated from adrenergically mediated atrial fibrillation. The former is considered to represent a form of lone atrial fibrillation affecting particularly males aged 40 to 50 years. The arrhythmic episodes manifest themselves most often during the night lasting from minutes to hours, whereas in adrenergic mediated atrial fibrillation, atrial fibrillation is often provoked by emotional or physical stress. (Hohnloser, van de Loo et al., 1994). Thus, hypertension (e.g., neurogenic hypertension) can be treated with burst stimulation of the left insula using the stimulation system of embodiments herein. In a similar fashion, bradycardia can be treated by burst stimulation of the right insula as subjects with bradycardia have significantly higher metabolic activity in the right (p<0.0001) and in the left temporal insula (p<0.015) than those with normal heart rates (Volkow, Wang et al., 2000). Lone atrial fibrillation can be treated by either by left or rightsided burst stimulation depending on whether it is vagally or adrenergicly induced.

Sleep Apnea

Activity in the sympathetic nervous system is enhanced not only in obstructive apnea, but also in central and mixed apnea (Shimizu, Takahashi et al., 1997). Burst rate during apnea is higher in central apneas than in obstructive apneas. Burst rate is the central component of mixed apnea and the obstructive component of mixed apneas (Shimizu, Takahashi et al., 1997). Thus, embodiments herein can be used to activate respiration during apneas by burst stimulation of the anterior insula.

CONCLUSION

One or more of the operations described above in connection with the methods may be performed using one or more processors. The different devices in the systems described herein may represent one or more processors, and two or more of these devices may include at least one of the same processors. In one embodiment, the operations described herein may represent actions performed when one or more processors (e.g., of the devices described herein) execute program instructions stored in memory (for example, software stored on a tangible and non-transitory computer readable storage medium, such as a computer hard drive, ROM, RAM, or the like).

The processor(s) may execute a set of instructions that are stored in one or more storage elements, in order to process data. The storage elements may also store data or other information as desired or needed. The storage element may be in the form of an information source or a physical memory element within the controllers and the controller device. The set of instructions may include various commands that instruct the controllers and the controller device to perform specific operations such as the methods and processes of the various embodiments of the subject matter described herein. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to user commands, or in response to results of previous processing, or in response to a request made by another processing machine.

The controller may include any processor-based or microprocessor-based system including systems using microcontrollers, reduced instruction set computers (RISC), application specific integrated circuits (ASICs), field-programmable gate arrays (FPGAs), logic circuits, and any other circuit or processor capable of executing the functions described herein. When processor-based, the controller executes program instructions stored in memory to perform the corresponding operations. Additionally or alternatively, the controllers and the controller device may represent circuits that may be implemented as hardware. The above examples are exemplary only, and are thus not intended to limit in any way the definition and/or meaning of the term "controller."

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions, types of materials and coatings described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 45 U.S.C. § 112(f), unless and until such claim limitations expressly use the phrase "means for" followed by a statement of function void of further structure.

What is claimed is:

1. A method of delivering electrical stimulation to nerve tissue of a patient, the method comprising:
operating a programmer device to define a composite pulse sequence for electrical stimulation of the patient, wherein the operating a programmer device comprises: (1) defining a first pulse train defined by at least a first frequency (2) defining a second pulse train defined by at least a second frequency, wherein the first and second frequencies are different, and (3) creating the composite pulse sequence by combining the first and second pulse trains by temporally shifting pulses of the first and second pulse trains to prevent pulses in the composite pulse sequence from overlapping in time, wherein the temporally shifting comprises applying repellant time shift factors between adjacent pulses of the first pulse train relative to the second pulse train, applying attractive time shift factors between adjacent pulses of the first pulse train, and applying attractive time shift factors between adjacent pulses of the second pulse train, wherein the programmer calculates a difference in timing between adjacent pulses for each of the first and second pulse trains and applies the attractive time shift factors for the first and second pulse trains as elastic forces proportional to the differences in timing between adjacent pulses;

communicating the composite pulse sequence from the programmer device to an implantable pulse generator (IPG) implanted in the patient;

operating the IPG to generate electrical pulses according to the composite pulse sequence; and applying the generated electrical pulses of the composite pulse sequence to nerve tissue of the patient using one or more electrodes of a stimulation lead implanted in the patient.

2. The method of claim 1 wherein the attractive time shift factors for the first pulse sequence and the attractive time shift factors for the second pulse sequence differ in magnitude for equal amounts of time for respective timing differences between adjacent pulses.

3. The method of claim 1 wherein the repellant time shift factors are applied in a manner that is non-linearly dependent upon timing between adjacent pulses.

4. The method of claim 1 wherein the first and second pulse sequences include a burst stimulation puke sequence with groups of pukes repeated at a burst frequency and a tonic stimulation puke sequence of individual pukes repeated at a single fixed frequency.

5. The method of claim 1 wherein the repellant and attractive time shift factors are applied in an iterative manner to define the composite pulse sequence.

* * * * *